(12) United States Patent
Cano et al.

(10) Patent No.: US 7,759,351 B2
(45) Date of Patent: Jul. 20, 2010

(54) OXAZOLIDINONE COMPOUNDS, AND COMPOSITIONS AND METHODS RELATED THERETO

(75) Inventors: Montserrat Cano, Monistrol (ES); Albert Palomer, Barcelona (ES); Antonio Guglietta, Barcelona (ES)

(73) Assignee: Ferrer Internacional, S.A., Barcelona (ES)

( * ) Notice: Subject to any disclaimer, the term of this patent is extended or adjusted under 35 U.S.C. 154(b) by 76 days.

(21) Appl. No.: 11/922,848

(22) PCT Filed: Jun. 26, 2006

(86) PCT No.: PCT/EP2006/063541

§ 371 (c)(1),
(2), (4) Date: Mar. 14, 2008

(87) PCT Pub. No.: WO2007/000432

PCT Pub. Date: Jan. 4, 2007

(65) Prior Publication Data

US 2009/0062266 A1  Mar. 5, 2009

(30) Foreign Application Priority Data

Jun. 27, 2005 (EP) .................. 05105714

(51) Int. Cl.
C07D 413/10 (2006.01)
A61K 31/496 (2006.01)
(52) U.S. Cl. ............... 514/253.04; 514/253.05; 514/253.06; 544/362; 544/363
(58) Field of Classification Search ........ 544/362, 544/363; 514/253.04, 253.05, 253.06
See application file for complete search history.

(56) References Cited

FOREIGN PATENT DOCUMENTS

| WO | WO-03/048136 A | 6/2003 |
|----|----------------|--------|
| WO | WO-2004/007489 A | 1/2004 |
| WO | WO-2004/089944 A | 10/2004 |

Primary Examiner—Kahsay T Habte
(74) Attorney, Agent, or Firm—Birch, Stewart, Kolasch & Birch, LLP

(57) ABSTRACT

The invention provides new oxazolidinone compounds of formula (I) wherein A is certain heterocycles optionally substituted; $R_1$, $R_2$, $R_3$ and $R_4$ are independently selected from —H and halogen; X is selected from O, S, $NR_9$ and $CR_9R_{10}$; $R_9$ and $R_{10}$ having different meanings; Y is selected from O, S, SO, $SO_2$, NO, $NR_{12}$ and $CR_{12}R_{13}$; $R_{12}$ and $R_{13}$ having different meanings. It also provides different processes for the preparation of such compounds. Oxazolidinone compounds of formula (I) are active against Gram-positive and some Gram-negative human and veterinary pathogens with a weak monoamine oxidase (MAO) inhibitory activity. They are useful for the treatment of bacterial infections.

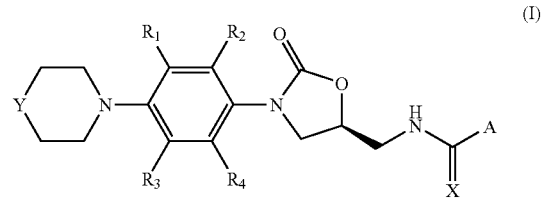

(I)

40 Claims, No Drawings

OXAZOLIDINONE COMPOUNDS, AND COMPOSITIONS AND METHODS RELATED THERETO

TECHNICAL FIELD

This invention is directed to oxazolidinone antimicrobial compounds, which are active against Gram-positive and some Gram-negative bacteria with a weak monoamine oxidase (MAO) inhibitory activity.

BACKGROUND OF THE INVENTION

Oxazolidinones are prominent among the new Gram-positive antimicrobial agents now becoming available. Oxazolidinones bind to the 50S subunit of the prokaryotic ribosome, preventing formation of the initiation complex for protein synthesis. This is a novel mode of action. Other protein synthesis inhibitors either block polypeptide extension or cause misreading of mRNA. Linezolid (N-[[(5S)-3-[3-fluoro-4-(4-morpholinyl)phenyl]-2-oxo-5-oxazolidinyl]methyl]acetamide) is the first approved antimicrobial oxazolidinone for clinical use in the United States and elsewhere.

Linezolid minimal inhibitory concentrations (MICs) vary slightly with the test mode, laboratory, and significance attributed to thin hazes of bacterial survival, but all workers find that the susceptibility distributions are narrow and unimodal with MIC values between 0.5 and 4 µg/mL for streptococci, enterococci and staphylococci. Full activity is retained against Gram-positive cocci resistant to other antibiotics, including methicillin-resistant staphylococci and vancomycin-resistant enterococci. MICs are 2-8 µg/mL for *Moxorella, Pasteurella* and *Bacteroides* spp. but other Gram-negative bacteria are resistant as a result of endogenous efflux activity as well as the intake presented by Gram-negative bacteria outer membrane cell.

Linezolid is indicated for the treatment of adult patients with the following infections:

nosocomial pneumonia caused by *Staphylococcus aureus* (methicillin-susceptible and -resistant strains) or *Streptococcus pneumoniae* (including multidrug-resistant strains [MDRSP]). MDRSP refers to isolates resistant to two or more of the following antibiotics: penicillins, second-generation cephalosporins, macrolides, tetracyclines, and trimethoprim/sulfamethoxazole;

complicated skin and skin structure infections, including diabetic foot infections, without concomitant osteomyelitis, caused by *Staphylococcus aureus* (methicillin-susceptible and -resistant strains), *Streptococcus pyogenes*, or *Streptococcus agalactiae*;

uncomplicated skin and skin structure infections caused by *Staphylococcus aureus* (methicillin-susceptible only) or *Streptococcus pyogenes*;

vancomycin-resistant *Enterococcus faecium* infections, including cases with concurrent bacteremia; and community-acquired pneumonia caused by *Streptococcus pneumoniae* (including multidrug-resistant strains [MDRSP]), also in cases with concurrent bacteremia, or caused by *Staphylococcus aureus* (methicillin-susceptible strains only).

Oxazolidinones were originally developed as MAO inhibitors for treatment of depression and Parkinson's disease. MAO is one of the primary enzymes responsible for the catabolism of catecholamines. In humans, MAO occurs in two isoforms, MAO-A and MAO-B. MAO-A preferentially deaminates serotonin (5-HT) and norepinephrine; MAO-B preferentially deaminates phenylethylamine, benzylamine, and, in man, dopamine. Normally MAO-A inhibitors, such as moclobemide or tranylcypromine, have been used as antidepressant agents while MAO-B inhibitors, such as selegiline, have been used preferably in the therapy of Parkinson's disease. U.S. Pat. No. 3,655,687 discloses 5-hydroxymethyl-3-substituted-2-oxazolidinone derivatives with significant antidepressant activity. A compound disclosed in this patent, toloxatone, 5-(hydroxymethyl)-3-(3-methylphenyl)-2-oxazoidinone, is of particular reference.

Toloxatone is a selective, reversible inhibitor of MAO-A and has been introduced in clinical practice. Because of this reason, particular attention has been paid to the question of whether evidence of adverse interaction with drugs known to be metabolized by monoamine oxidase would occur in patients treated with linezolid. An enhanced pressor response has been seen in patients taking certain adrenergic agents, including phenylpropanolamine and pseudoephedrine, and it is specifically noted that the doses of these drugs should be reduced in patients receiving linezolid. Animal studies suggest that linezolid moderately potentiates the pressor effects of the endogenous and dietary amine, tyramine, and other sympathomimetic amines. The package insert for linezolid warns against combining it with tyramine-rich foods and about being aware of a potential interaction with adrenergic and serotonergic agents. Accordingly, there is a need of new oxazolidinone antimicrobial compounds with minimum MAO inhibitory activity to eliminate the related side effects from potential drug-drug interactions.

The preparation of linezolid is disclosed in PCT application WO 9507271.

PCT application WO 03084534 discloses a method for treating a diabetic foot infection with oxazolidinones, specially with 3-{4-[1-(2,3-dihydroxy-propionyl)-1,2,3,6-tetrahydro-pyridin-4-yl]-3,5-difluoro-phenyl}-5-(isoxazol-3-ytoxymethyl)-oxazolidin-2-one; 2,2-difluoro-N-({(5S)-3-[3-fluoro-4-(4-glycoloyl-piperazin-1-yl)phenyl]-2-oxo-1,3-oxazolidin-5-yl}methyl)ethanethioamide; and linezolid.

PCT application WO 03063862 discloses a method of treating a patient in need of oxazolidinone by administering an effective amount of oxazolidinone and an effective amount of at least one vitamin selected from the group consisting of vitamin B2, vitamin B6, vitamin B12 and folic acid. Patent applications DE 10105989 and US 2003/0153610 disclose the preparation of the N-((2-oxo-3-phenyl-1,3-oxazolidin-5-yl)-methyl)-heterocyclic amides and their use for inhibiting blood coagulation in vitro, especially in preserved blood or biological samples containing factor Xa. Heterocyclic amides disclosed in US 2003/0153610 are limited to thienyl amides, while DE 10105989 focuses on N-[[3-[(4-substituted)-phenyl]-2-oxo-5-oxazolidinyl]methyl]-amides with substituents containing either the oxo- or N-oxide moiety. Moreover, these documents describe neither antibacterial nor MAO inhibitory activity.

WO 04007489 describes some oxazolidinone derivatives having antibacterial activity against Gram-positive and Gram-negative bacteria. In this patent application some of the limitations which appeared during the clinical development and use of linezolid and its potential congeners were pointed out: It is said that this class of compounds has a propensity to induce myelosuppresion with consequent thrombocytopenia and that the inhibition of monoamine oxidase by oxazolidinones has prompted clinicians to recommend the use of members of this class with caution during concomitant usage of adrenergic or serotonergic agents and selective serotonin reuptake inhibitors.

WO 04089944 describes certain substituted phenyl oxazolidinones which are useful antimicrobial agents against a number of human and veterinary pathogens, including gram positive aerobic bacteria as well as anaerobic organisms. In this document, no mention is made about the inhibitory activity of the monoamine oxidase.

Thus, it is apparent that, despite all the research efforts made in the past, there is still a need to find new effective antibacterial agents, having low side effects than those known in the art.

SUMMARY OF THE INVENTION

Inventors have found that compounds of the class disclosed in the present application are particularly active antimicrobial agents showing a weak MAO inhibitory activity, which imply a significant reduction of the related side effects from potential drug-drug interactions. This is surprising, since the inhibition of monoamine oxidase by oxazolidinones is known to produce several side effects and, therefore, the skilled person would not search for antibacterial agents with low or no side effects at all among the oxazolidinone derivatives. Furthermore, compounds of the present invention show a selective activity against *Staphylococcus* bacteria, compared with *Enterococcus* bacteria, which is a valuable property in the treatment of diseases which need a specific antibiotic against *Staphylococcus* such as community-acquired methicillin-resistant *Staphylococcus aureus* (CA-MRSA) infections, which are gaining a foothold in the community and seem to be trending towards epidemic levels in the US according to last studies On the whole the present invention provides evidence that new N-[[(3-[4-substituted-phenyl]-2-oxo-5-oxazolidinyl] methyl]-amine compounds are specifically active against Gram-positive human and veterinary pathogens, in particular are active against *Staphylococcus* bacteria, with a weak monoamine oxidase inhibitory activity.

The present invention describes a novel class of oxazolidinone compounds represented by formula (I):

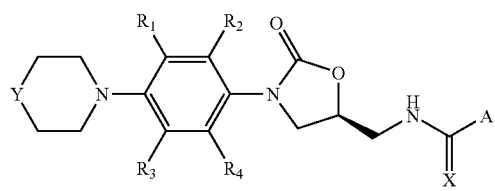

(I)

or a pharmaceutically acceptable salt thereof, wherein A, $R_1$, $R_2$, $R_3$, $R_4$, X and Y are defined below, which are antibacterial agents specifically active against Gram-positive and some Gram-negative human and veterinary pathogens with a weak monoamine oxidase (MAO) inhibitory activity.

It is another object of this invention to provide synthetic procedures for preparing said compounds. Another object of this invention relates to the use of a compound of formula (I) or a pharmaceutically acceptable salt thereof, for the preparation of a medicament for the treatment of bacterial infections in a mammal, including a human. The last aspect may alternatively be formulated as a method to treat a mammal, including a human, suffering from a bacterial infection by administering a therapeutically effective amount of a compound of formula (I) or a pharmaceutically acceptable salt thereof

DETAILED DESCRIPTION OF THE INVENTION

The present invention relates to novel oxazolidinone compounds of formula (I):

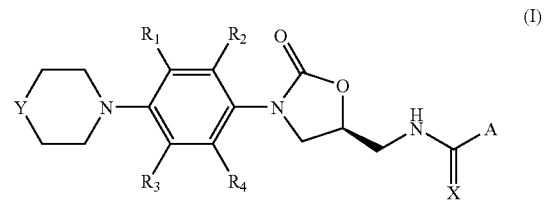

(I)

wherein
$R_1$, $R_2$, $R_3$ and $R_4$ are independently selected from —H and halogen;
A is selected from the group consisting of

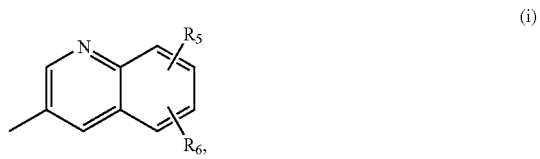

(i)

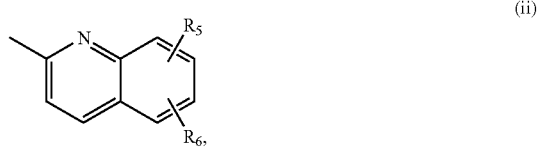

(ii)

(iii)

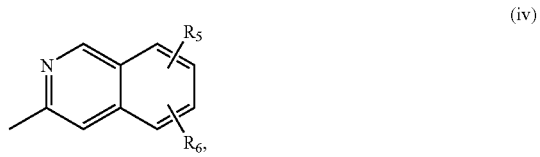

(iv)

(v)

(vi)

-continued

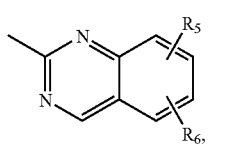 (vii)

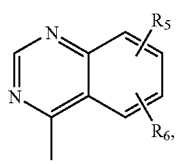 (viii)

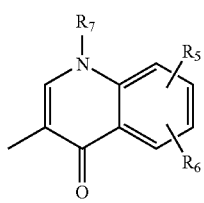 (ix)

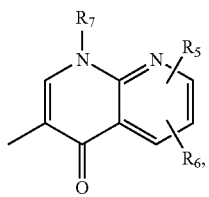 (x)

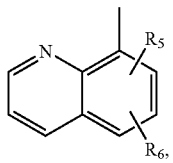 (xi)

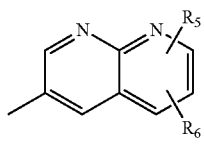 (xii)

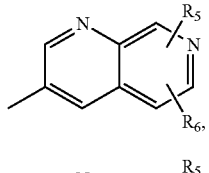 (xiii)

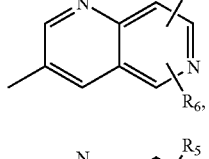 (xiv)

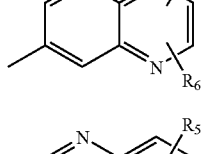 (xv)

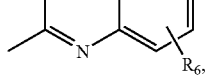 (xvi)

-continued

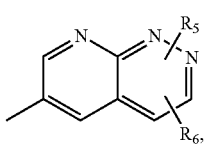 (xvii)

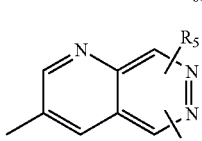 (xviii)

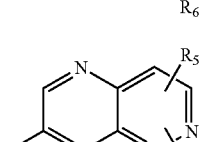 (xix)

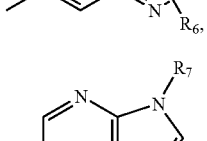 (xx)

and

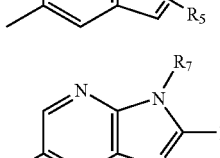 (xxi)

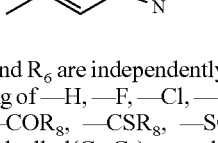

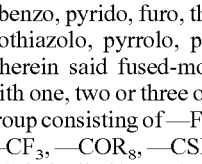

$R_5$ and $R_6$ are independently selected from the group consisting of —H, —F, —Cl, —Br, —OH, —NO$_2$, —CN, —CF$_3$, —COR$_8$, —CSR$_8$, —SO$_2$R$_8$, —OCOR$_8$, alkyl(C$_1$-C$_6$), haloalkyl(C$_1$-C$_6$), cycloalkyl(C$_3$-C$_6$), alkenyl(C$_2$-C$_6$), alkynyl(C$_2$-C$_6$), alkoxy(C$_1$-C$_6$), alkoxy(C$_1$-C$_6$)alkyl(C$_1$-C$_6$), —N—R$_{21}$R$_{22}$ and T; or $R_5$ and $R_6$ taken together form a benzo, pyrido, furo, thieno, oxazolo, isoxazolo, thiazolo, isothiazolo, pyrrolo, pyrazolo or imidazo fused-moiety, wherein said fused-moieties in turn may be substituted with one, two or three of the substituents selected from the group consisting of —F, —Cl, —Br, —OH, —NO$_2$, —CN, —CF$_3$, —COR$_8$, —CSR$_8$, —SO$_2$R$_8$, —OCOR$_8$, alkyl(C$_1$-C$_6$), haloalkyl(C$_1$-C$_6$), cycloalkyl(C$_3$-C$_6$), alkenyl(C$_2$-C$_6$), alkynyl(C$_2$-C$_6$), alkoxy(C$_1$-C$_6$), alkoxy(C$_1$-C$_6$)alkyl(C$_1$-C$_6$) and —N—R$_{21}$R$_{22}$, or a fused-ring selected from cyclopento, cyclohexo, cyclohepto, methylenedioxy and ethylenedioxy, wherein said fused-ring in turn may be substituted by one, two or three of the substituents selected from the group consisting of alkyl(C$_1$-C$_6$), cycloalkyl(C$_3$-C$_6$), alkenyl(C$_2$-C$_6$) and alkynyl(C$_2$-C$_6$);

$R_7$ is selected from the group consisting of —H, optionally substituted alkyl(C$_1$-C$_6$), cycloalkyl(C$_3$-C$_6$), alkenyl(C$_2$-C$_6$), alkynyl(C$_2$-C$_6$), alkoxy(C$_1$-C$_6$), —N—R$_{21}$R$_{22}$ and T; or $R_7$ and $R_5$ or $R_6$ taken together form where possible a ring of 2 to 6 carbon atoms and containing from 1 to 3 groups selected from O, N, S, SO and SO$_2$, which in turn may be substituted by one, two or three of the substituents selected from the group consisting of alkyl(C$_1$-C$_6$), cycloalkyl(C$_3$-C$_6$), alkenyl(C$_2$-C$_6$) and alkynyl(C$_2$-C$_6$);

$R_8$ is selected from the group consisting of —H, alkyl(C$_1$-C$_6$), cycloalkyl(C$_3$-C$_6$), alkenyl(C$_2$-C$_6$), alkynyl(C$_2$-C$_6$), alkoxy(C$_1$-C$_6$), alkoxy(C$_1$-C$_6$)alkyl(C$_1$-C$_6$), hydroxyalkyl(C$_1$-C$_6$), —N—R$_{21}$R$_{22}$ and T;

$R_9$ and $R_{10}$ are independently selected from the group consisting of —H, —CN, —NO$_2$, —COR$_{11}$, —SO$_2$R$_{11}$, alkyl ($C_1$-$C_6$), haloalkyl($C_1$-$C_6$), cycloalkyl($C_3$-$C_6$), alkenyl ($C_2$-$C_6$), alkynyl($C_2$-$C_6$), alkoxy($C_1$-$C_6$), alkoxy($C_1$-$C_6$)alkyl($C_1$-$C_6$), —N—$R_{21}R_{22}$ and T;

$R_{11}$ is selected from the group consisting of —H, —OH, alkyl($C_1$-$C_6$), haloalkyl($C_1$-$C_6$), cycloalkyl($C_3$-$C_6$), alkenyl($C_2$-$C_6$), alkynyl($C_2$-$C_6$), alkoxy($C_1$-$C_6$)alkyl($C_1$-$C_6$) and T;

$R_{12}$ and $R_{13}$ are independently selected from the group consisting of —H, —OH, —$CHR_{14}R_{15}$, —CN, —$COR_{14}$, —$CSR_{14}$, —$COOR_{14}$, —$CSOR_{14}$, —$CONR_{14}R_{15}$, —$CSNR_{14}R_{15}$, —$CON(R_{16})N(R_{14})R_{15}$, —$SO_2R_{14}$, —$SO_2OR_{14}$, —$SO_2NR_{14}R_{15}$, alkyl($C_1$-$C_6$), haloalkyl($C_1$-$C_6$), cycloalkyl($C_3$-$C_6$), alkenyl($C_2$-$C_6$), alkynyl($C_2$-$C_6$), alkoxy($C_1$-$C_6$)alkyl($C_1$-$C_6$) and T;

$R_{14}$ and $R_{15}$ are independently selected from the group consisting of —H, —OH, —$COR_{16}$, —$CSR_{16}$, —$SO_2R_{16}$, —$NR_{17}R_{18}$, optionally substituted alkyl($C_1$-$C_6$), cycloalkyl($C_3$-$C_6$), alkenyl($C_2$-$C_6$), alkynyl($C_2$-$C_6$), alkoxy($C_1$-$C_6$), phenyl,

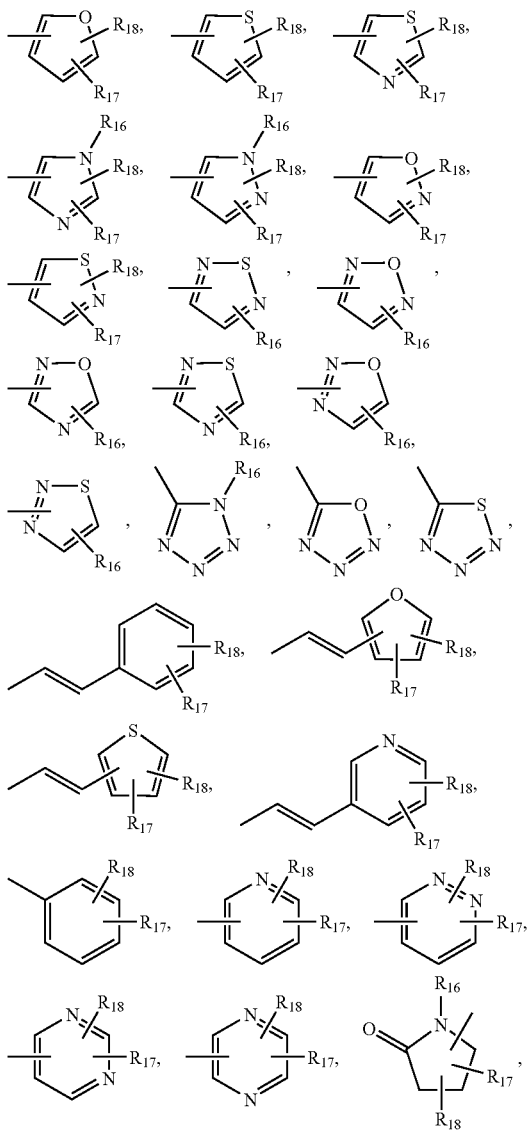

-continued

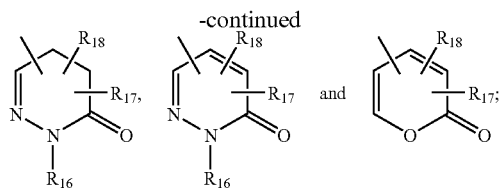

$R_{16}$ is —H, —OH, alkyl($C_1$-$C_6$), cycloalkyl($C_3$-$C_6$), alkenyl ($C_2$-$C_6$), alkynyl($C_2$-$C_6$), alkoxy($C_1$-$C_6$), alkoxy($C_1$-$C_6$) alkyl($C_1$-$C_6$), hydroxyalkyl($C_1$-$C_6$) and T;

$R_{17}$ and $R_{18}$ are independently selected from the group consisting of —H, —OH, —F, —Cl, —Br, —$NO_2$, —CN, —$NR_{19}R_{20}$, —$COR_{19}$, —$CONR_{19}R_{20}$, —$SO_2R_{19}$, —$SO_2NR_{19}R_{20}$, optionally substituted alkyl($C_1$-$C_6$), cycloalkyl($C_3$-$C_6$), alkenyl($C_2$-$C_6$), alkynyl($C_2$-$C_6$), alkoxy($C_1$-$C_6$) and T; or $R_{17}$ and $R_{18}$ taken together form a benzo-fused moiety, which in turn may be substituted with one, two or three of the substituents selected from the group consisting of —F, —Cl, —Br, —OH, —$NO_2$, —CN, —$CF_3$, —$COR_8$, —$CSR_8$, —$SO_2R_8$, —$OCOR_8$, alkyl($C_1$-$C_6$), haloalkyl($C_1$-$C_6$), cycloalkyl($C_3$-$C_6$), alkenyl($C_2$-$C_6$), alkynyl($C_2$-$C_6$), alkoxy($C_1$-$C_6$), alkoxy($C_1$-$C_6$)alkyl($C_1$-$C_6$) and —N—$R_{21}R_{22}$, or a fused-ring selected from cyclopento, cyclohexo, cyclohepto, methylenedioxy and ethylenedioxy, wherein said fused-ring in turn may be substituted by one, two or three of the substituents selected from the group consisting of alkyl($C_1$-$C_6$), cycloalkyl($C_3$-$C_6$), alkenyl($C_2$-$C_6$) and alkynyl($C_2$-$C_6$);

$R_{19}$ and $R_{20}$ are independently selected from the group consisting of —H, —OH, optionally substituted alkyl($C_1$-$C_6$), cycloalkyl($C_3$-$C_6$), alkenyl($C_2$-$C_6$), alkynyl($C_2$-$C_6$), alkoxy($C_1$-$C_6$) and T;

$R_{21}$ and $R_{22}$ are independently selected from —H, alkyl($C_1$-$C_6$), cycloalkyl($C_3$-$C_6$), alkenyl($C_2$-$C_6$), alkynyl($C_2$-$C_6$) and T, said —N—$R_{21}R_{22}$ groups may represent a heterocyclic ring selected from the group consisting of pyrrolidinyl, piperidinyl, piperazinyl optionally N-substituted by alkyl($C_1$-$C_6$), cycloalkyl($C_3$-$C_6$), alkenyl($C_2$-$C_6$) or alkynyl($C_2$-$C_6$), morpholinyl, thiomorpholinyl, thiomorpholinyl S-oxide and thiomorpholinyl S-dioxide;

T represents a phenyl or heteroaryl group each optionally substituted, wherein heteroaryl is selected from the group consisting of pyridine, pyridazine, pyrimidine, pyrazine, furan, thiophene, oxazole, thiazole, imidazole, pyrazole, isoxazole, isothiazole, 1,2,5-thiadiazole, furazan, 1,2,4-oxadiazole, 1,2,4-thiadiazole, 1,2,3-oxadiazole, 1,2,3-thiadiazole, tetrazole, 1,2,3,4-oxatriazole and 1,2,3,4-thiatriazole, wherein substituents optionally present on the optionally substituted phenyl or optionally substituted heteroaryl group may be one, two or three of the substituents selected from the group consisting of —F, —Cl, —Br, —OH, —$NH_2$, —$NO_2$, —CN, —$CF_3$, —$COR_8$, —$CSR_8$, —$SO_2R_8$, —$OCOR_8$, alkyl($C_1$-$C_6$), haloalkyl($C_1$-$C_6$), cycloalkyl($C_3$-$C_6$), alkenyl($C_2$-$C_6$), alkynyl($C_2$-$C_6$), alkoxy($C_1$-$C_6$), alkoxy($C_1$-$C_6$)alkyl($C_1$-$C_6$), NH-alkyl ($C_1$-$C_6$), NH-cycloalkyl($C_3$-$C_6$), —N-dialkyl($C_1$-$C_6$), —N-(alkyl($C_1$-$C_6$))(cycloalkyl($C_3$-$C_6$)), methylenedioxy, ethylenedioxy and a heterocyclic ring selected from the group consisting of pyrrolidinyl, piperidinyl, piperazinyl optionally N-substituted by alkyl($C_1$-$C_6$), cycloalkyl($C_3$-$C_6$), alkenyl($C_2$-$C_6$) or alkynyl($C_2$-$C_6$), morpholinyl, thiomorpholinyl, thiomorpholinyl S-oxide and thiomorpholinyl S-dioxide;

X is selected from O, S, NR$_9$ and CR$_9$R$_{10}$; and

Y is selected from O, S, SO, SO$_2$, NO, NR$_{12}$ and CR$_{12}$R$_{13}$; and wherein the optional substituents of the alkyl(C$_1$-C$_6$) groups might be one, two or three selected from the group consisting of —F, —Cl, —NO$_2$, —OR$_{21}$, —COR$_{21}$, —N—R$_{21}$R$_{22}$, oxo, cycloalkyl(C$_3$-C$_6$), alkenyl(C$_2$-C$_6$), alkynyl(C$_2$-C$_6$), —CN, T, —COO—R$_{21}$, —OCOR$_{21}$, —CON—R$_{21}$R$_{22}$, —N(R$_{21}$)—CO—R$_{22}$, —OCON—R$_{21}$R$_{22}$, and —N(R$_{21}$)—COO—R$_{22}$;

or a pharmaceutically acceptable salt thereof.

Preferably, the present invention relates to new oxazolidinones of formula (I) wherein R$_1$ is —F; R$_2$, R$_3$ and R$_4$ are each —H; X is O, S and N—CN; Y is O, S, SO, SO$_2$ and NR$_{12}$; A is a quinoline group selected from

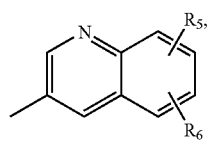

(i)

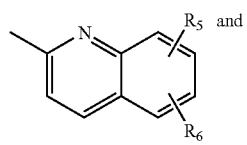

(ii) and

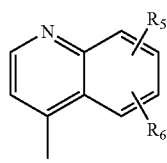

(iii)

wherein R$_5$ and R$_6$ are each —H; or R$_5$ is methyl and R$_6$ is methoxy; or R$_5$ and R$_6$ are selected from the group consisting of —F, —Cl and —Br; and R$_{12}$ is selected from the group consisting of —H, methyl, ethyl, —CN, —COCH$_2$CN, —COCH$_3$, —COOCH$_3$, —CONHCH$_3$, —SO$_2$CH$_3$, —SOCH$_3$, —SO$_2$NHCH$_3$,

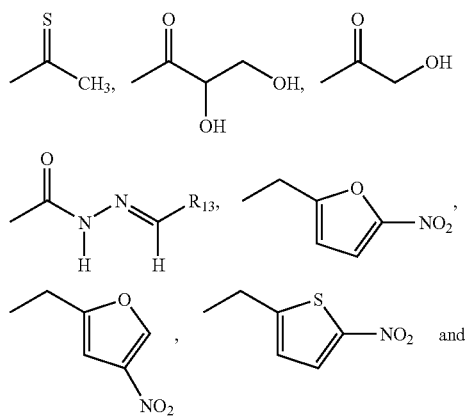

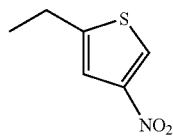

wherein R$_{13}$ is selected from the group consisting of —H, methyl, ethyl, isopropyl, tertbutyl, —CH$_2$OH, —CH$_2$NH$_2$, —COOH, —COOCH$_3$, —COOC$_2$H$_5$, —CH$_2$Cl, —CONH$_2$, —CH$_2$—CH═CH$_2$, —CH$_2$—C≡CH, —CH═CH$_2$, —C≡CH and —CH═CHN(CH$_3$)$_2$.

The term "pharmaceutically acceptable salts" used herein encompasses any salt formed from organic and inorganic acids, such as hydrobromic, hydrochloric, phosphoric, nitric, sulfuric, acetic, adipic, aspartic, benzenesulfonic, benzoic, citric, ethanesulfonic, formic, fumaric, glutamic, lactic, maleic, malic, malonic, mandelic, methanesulfonic, 1,5-naphthalenedisulfonic, oxalic, pivalic, propionic, p-toluenesulfonic, succinic, tartaric acids and the like.

The compounds are useful antimicrobial agents, effective against a number of human and veterinary microorganisms. Example 43 illustrates that compounds of the present invention exhibit a weak MAO inhibitory activity, which indicates that these compounds possess the ability to minimize or eliminate potential drug-drug interactions since strong inhibition of monoamine oxidase can result in altered clearance rates for other compounds normally metabolized by monoamine oxidase, including several pharmaceuticals. In addition, it is of particular relevance to avoid increased levels of neurotransmitter amines, such as dopamine, serotonin and noradrenaline.

Example 43 also illustrates that compounds of the present invention display a selective activity against *Staphylococcus* bacteria in comparison with *Enterococcus* bacteria. This property is clearly shown by those compounds in the present invention which contain a quinoline-type structure, in contrast to those compounds which contain other heterocycles, such as those described in WO 04089944. For instance, compound of Example 34 of the present invention is 100 times more active in *Staphylococcus* than in *Enterococcus*. The selectivity is a valuable property in the treatment of diseases which need a specific antibiotic treatment for *Staphylococcus*. Among them are the infections produced by *S. aureus* such as furunculosis, cellulitis, pyemia, pneumonia, osteomyelitis, endocarditis, suppuration of wounds, and food poisoning; infections produced by *S. epidermidis* such as small stitch abscesses and other skin wounds, which occurs on parasitic skin and mucous membranes of man and other animals; *S. hycius* such as greasy pig disease; *S. pyogenes albus* and *S. pyogenes aureus*. Therefore, these compounds are useful antimicrobial agents, effective against a number of human and veterinary microorganisms with advantages over the known in the art.

Preferred compounds are the enantiomers having the S-configuration at C-5 position of the oxazolidinone ring.

The preferred compounds of the present invention are:
(a) 7-Methoxy-2-methyl-N-[[(5S)-3-[3-fluoro-4-(4'-acetyl-4-piperazinyl)phenyl]-2-oxo-5-oxazolidinyl]methyl]-3-quinolinecarboxamide, of formula:

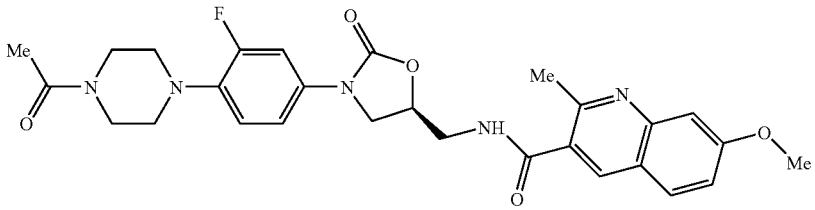

(b) 7-Methoxy-2-methyl-N-[[(5S)-3-[3-fluoro-4-(4-morpholinyl)-phenyl]-2-oxo-5-oxazolidinyl]methyl]-3-quinolinecarboxamide, of formula:

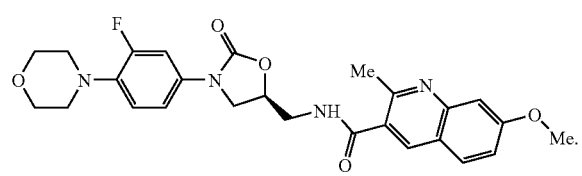

(c) 7-Methoxy-2-methyl-N-[[(5S)-3-[3-fluoro-4-(4-thiomorpholinyl)-phenyl]-2-oxo-5-oxazolidinyl]methyl]-3-quinolinecarboxamide, of formula:

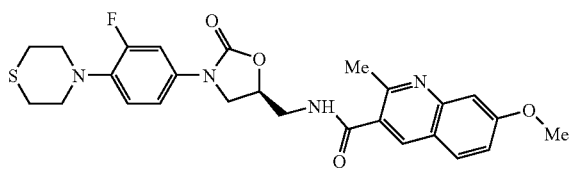

and
(d) 7-Methoxy-2-methyl-N-[[(5S)-3-[3-fluoro-4-(4'-thioacetyl-4-piperazinyl)phenyl]-2-oxo-5-oxazolidinyl]methyl]-3-quinolinecarboxithioamide, of formula:

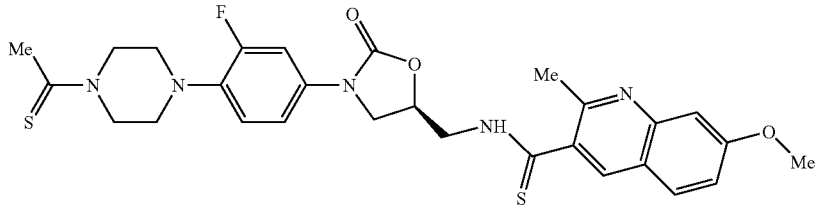

The compounds of the general formula (I) may be prepared by several different methods, depending on the nature of the functional groups:

a) Preparation of Amide Compounds (I, X=O):

Formally amides are prepared by reacting an amino methyl intermediate of general formula (II) with an activated form of the corresponding acid of formula (III):

wherein A, $R_1$, $R_2$, $R_3$, $R_4$ and Y are as defined above. The activated form of the acid (III) is selected from the group consisting of acid halides, imidazolides, p-nitrophenyl esters and 2,4,5-trichlorophenyl esters thereof. Other activated forms of the acid (III) are prepared In situ in the presence of a reagent selected from triphenylphosphine, bromotrichloromethane, dicyclohexylcarbodiimide, 2-chloropyridinium cation, 3-chloroisoxazolium cation, diphenylphosphoryl azide, N-hydroxybenzotriazole, 2-(1H-benzotriazole-1-yl)-1,1,3,3-tetramethyluronium hexafluorophosphate, 1-mesitylene-2-sulfonyl)-3-nitro-1H-1,2,4-triazole, benzotriazole-1-yl-oxy-trispyrrolidino-phosphonium hexafluorophosphate, 1-ethyl-3-(3'-dimethylaminopropyl)carbodiimide hydrochloride and 2-(1H-benzotriazole-1-yl)-1,1,3,3-tetramethyluronium tetrafluoroborate.

b) Preparation of Thioamide Compounds (I, X=S):

The preparation of the thioamide compounds (I, X=S) from the corresponding amide compounds (I, X=O) can be performed by several thionation reagents selected from:

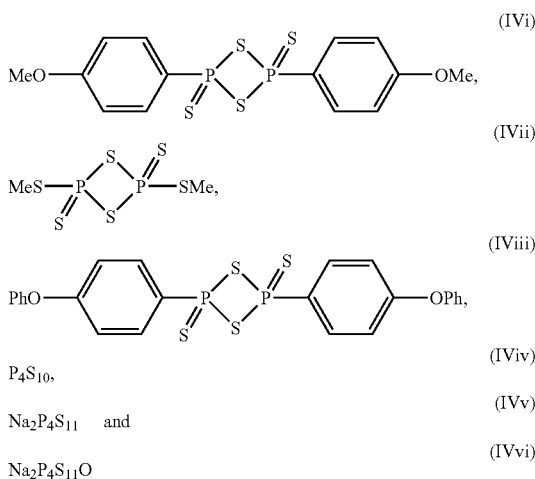

(IVi)

(IVii)

(IViii)

P$_4$S$_{10}$, (IViv)

Na$_2$P$_4$S$_{11}$ and (IVv)

Na$_2$P$_4$S$_{11}$O (IVvi)

The thionation reagent preferred is (IVi), known as Lawesson's reagent.

Otherwise, the thioamide compounds can be obtained by condensation of the corresponding amino methyl derivative (II) with an alkyldithioamide (IIIi):

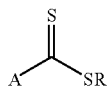

(IIIi)

wherein A is as defined in the general formula (I) and R is an alkyl(C$_1$-C$_6$).

c) Preparation of Sulfoxide Compounds (I, Y=SO):

The preparation of the sulfoxide compounds (I, Y=SO) can be performed from the corresponding compounds of general formula (I, Y=S), with several oxidizing reagents selected from the group consisting of sodium metaperiodate, hypervalent iodine reagents, chromic acid in acetic acid, chromic acid in pyridine, lead tetraacetate, manganese dioxide, thallium (III) nitrate and ozone, and the like, preferably sodium metaperiodate.

d) Preparation of Sulfone Compounds (I, Y=SO$_2$):

The preparation of sulfone compounds (I, Y=SO$_2$) from the corresponding sulfide (I, Y=S) can be performed by several oxidizing reagents such as an excess of hydrogen peroxide in acetic acid and catalytic osmium tetraoxide in the presence of N-methylmorpholine N-oxide. An excess of hydrogen peroxide in acetic acid is preferred.

e) Preparation of Cyanoamidine Compounds (I, X=N—CN):

The cyanoamidine compounds (I, X=N—CN) are synthesized by reacting the corresponding amino methyl derivative (II), with a cyanoimidate of general formula (V):

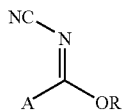

(V)

wherein A is as defined in the general formula (I) and R is an alkyl(C$_1$-C$_6$).

Certain amino methyl intermediates of general formula (II) are known in the art and may be prepared according to methods disclosed in the literature. Thus, PCT application WO 9507271 discloses the preparation of N-[[(5S)-3-[3-fluoro-4-(4-morpholinyl)-phenyl]-2-oxo-5-oxazolidinyl]-methyl]amine (II, R$_1$=F, R$_2$=R$_3$=R$_4$=H, Y=O), PCT application WO 9854161 discloses the preparation of N-[[(5S)-3-[3-fluoro-4-(4-thiomorphotinyl)-phenyl]-2-oxo-5-oxazotidinyt]methyl]amine (II, R$_1$=F, R$_2$=R$_3$=R$_4$=H, Y=S) and PCT application WO 0032599 discloses the preparation of N-[[(5S)-3-[3-fluoro-4-(4'-acetyl-4-piperazinyl)-phenyl]-2-oxo-5-oxazolidinyt]methyl]amine (II, R$_1$=F, R$_2$=R$_3$=R$_4$=H, Y=CH$_3$—CON). PCT application WO 04/018439 discloses the preparation of (S)—N-[3-[3-fluoro-4-[N-t-butoxycarbonylpiperazin-1-yl]phenyl]-2-oxooxazolidin-5-ylmethyl]azide and (S)-[3-[3-fluoro-4-[N-t-butoxycarbonylpiperazin-1-yl]phenyl]-2-oxooxazotidin-5-ylmethyl]alcohol.

The compounds of the present invention can be normally formulated in accordance with standard pharmaceutical practice as a pharmaceutical composition.

Another aspect of the invention relates to a pharmaceutical composition comprising a therapeutically effective amount of the compound of general formula (I) as defined above, together with the appropriate amounts of pharmaceutical excipients or carriers.

The pharmaceutical compositions of this invention may be administered in standard manner for the disease condition that it is desired to treat, for example by oral, parenteral, inhalatory, rectal, transdermal or topical administration. For these purposes the compounds of this invention may be formulated by means known in the art in the form of, for example, tablets, capsules, syrups, aqueous or oily solutions or suspensions, emulsions, dispersible powders, inhalatory solutions, suppositories, ointments, creams, drops and sterile aqueous or oily solutions or suspensions for injection and the like. The pharmaceutical compositions may contain flavoring agents, sweeteners, etc. in suitable solid or liquid carriers or diluents, or in a suitable sterile media to form suspensions or solutions suitable for intravenous, subcutaneous or intramuscular injection. Such compositions typically contain from 1 to 40%, preferably 1 to 10% by weight of active compound, the remainder of the composition being pharmaceutically acceptable carriers, diluents, solvents and the like.

The compounds of formula (I) are administered in an amount of 0.1 to 100 mg/kg of body weight/day, preferably 1 to 50 mg/kg of body weight/day.

The compounds of the present invention are useful in the treatment of conditions such as nosocomial *pneumoniae*, community acquired *pneumoniae*, caused by methicillin-resistant *Staphylococcus aureus* (MRSA), including concurrent bacteremia, penicillin resistance and sensitive *streptococcus pneumoniae*, diabetic foot infections and skin and skin structure infections, and all other infections caused by bacteria sensitive to the compounds described in the invention. The compounds of the present invention are effective against a number of human or animal pathogens, clinical isolates, including vancomycin-resistant organisms and methicillin-resistant organisms.

The following non-limiting examples illustrate the scope of the present invention.

EXAMPLES

Certain abbreviations used herein are defined as follows: "DCM" for dichloromethane, "DMAP" for 4-(dimethylamino)pyridine, "DMSO" for dimethylsulfoxide, "EDCI" for 3-dimethylaminopropyl-3-ethyl-carbodiimide hydrochloride, "ESI" for electro spray ionisation, "HOBt" for N-hydroxybenzotriazole, "HPLC" for high performance liquid chromatography, "MS" for mass spectroscopy and "TLC" for thin layer chromatography.

Example 1

7-methoxy-2-methyl-N-[[(5S)-3-[3-fluoro-4-(4-morpholinyl)phenyl]-2-oxo-5-oxazolidinyl]methyl]-3-quinolinecarboxamide

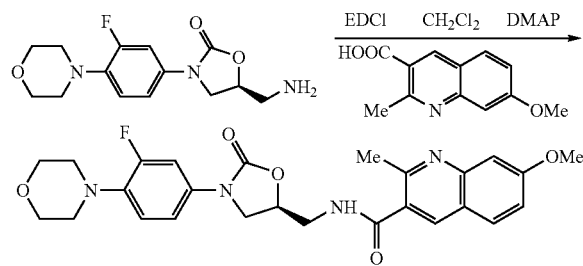

A solution of 110 mg (1.5 eq) of 7-methoxy-2-methylquinoline-3-carboxytic acid, 21 mg (0.5 eq) of DMAP and 97 mg of 1-ethyl-3-(3'-dimethylaminopropyl)carbodiimide hydrochloride (1.5 eq) in 5 mL of DCM was stirred at room temperature under argon for 30 minutes. Then, 100 mg (1 eq) of N-[[(5S)-3-[3-fluoro-4-(4-morpholinyl)-phenyl]-2-oxo-5-oxazolidinyl]methyl]amine were added in 5 mL of DCM and stirring was continued for 12 hours when complete conversion of the starting amine was observed by TLC. The crude mixture was washed with 5% HOAc solution, saturated NaHCO$_3$ and brine. The combined organic layers were dried (MgSO$_4$) and concentrated in vacuum to afford 173 mg of the title product (Yield=95%).

$^1$H NMR (400 MHz, δ, ppm, CDCl$_3$): 2.75 (3H, s), 3.03 (4H, m), 3.85 (4H, m), 3.9 (m, 3H), 3.94 (3H, s), 4.13 (1H, t, J=9.2 Hz), 4.92 (1H, m), 6.52 (1H, t, NH), 6.89 (1H, t, J=8.8 Hz), 7.09 (1H, dd, J=2.4, 8.4 Hz), 7.17 (1H, dd, J=2.8, 9.2 Hz), 7.33 (1H, d, J=2.4 Hz), 7.46 (1H, dd, J=2.8, 14.4 Hz), 7.61 (1H, d, J=9.2 Hz), 8.0 (1H, s).

HPLC (t, %): 8.9 min, 99%.
MS (ESI) m/z=495 (M+1)

Example 2

7-methoxy-2-methyl-N-[[(5S)-3-[3-fluoro-4-(4-thiomorpholinyl)phenyl]-2-oxo-5-oxazolidinyl]methyl]-3-quinolinecarboxamide

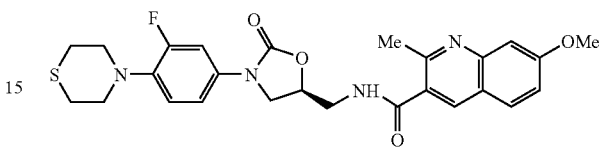

It was prepared following the same procedure as in Example 1, starting from 370 mg of 7-methoxy-2-methylquinoline-3-carboxylic acid and 350 mg of N-[[(5S)-3-[3-fluoro-4-(4-thiomorpholinyl)-phenyl]-2-oxo-5-oxazolidinyl]methyl]amine. After similar work-up, 244 mg were obtained corresponding to the desired 7-methoxy-2-methyl-N-[[(5S)-3-[3-fluoro-4-(4-thiomorpholinyl)-phenyl]-2-oxo-5-oxazolidinyl]methyl]-3-quinolinecarboxamide (Yield=43%).

$^1$H NMR (400 MHz, δ, ppm, CDCl$_3$): 2.69 (3H, s), 2.78 (4H, m), 2.23 (4H, m), 3.86 (m, 3H), 3.90 (3H, s), 4.05 (1H, t, J=8.8 Hz), 4.88 (1H, m), 6.82 (1H, t, J=8.8 Hz), 6.97 (1H, m), 7.07 (1H, dd, J=2.4, 8.8 Hz), 7.31 (1H, dd, J=3.2, 14 Hz), 7.34 (1H, d, J=2 Hz), 7.49 (2H, d, J=8.8 Hz), 8.0 (1H, s).

HPLC (t, %): 12.0 min, 99%.
MS (ESI) m/z=511 (M+1)

Example 3

7-methoxy-2-methyl-N-[[(5S)-3-[3-fluoro-4-(4'-acetyl-4-piperazinyl)-phenyl]-2-oxo-5-oxazolidinyl]methyl]-3-quinolinecarboxamide

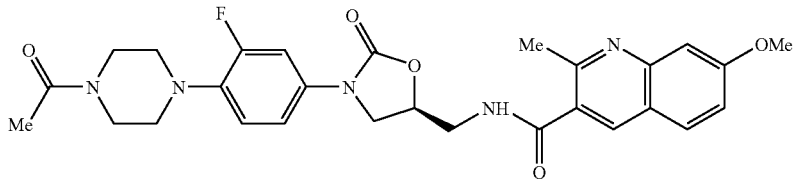

It was prepared following the same procedure as in Example 1, starting from 190 mg (1.5 eq) of 7-methoxy-2-methylquinoline-3-carboxylic acid and 200 mg (1 eq) of N-[[(5S)-3-[3-fluoro-4-(4'-acetyl-4-piperazinyl)-phenyl]-2-oxo-5-oxazolidinyl]methyl]amine. After similar work-up, 120 mg were obtained corresponding to the desired 7-methoxy-2-methyl-N-[[(5S)-3-[3-fluoro-4-(4'-acetyl-4-piperazinyl)-phenyl]-2-oxo-5-oxazolidinyl]methyl]-3-quinolinecarboxamide (Yield=38%).

$^1$H NMR (400 MHz, δ, ppm, CDCl$_3$): -2.69 (3H, s), 2.91 (2H, m), 2.98 (2H, m), 3.57 (2H, m), 3.70 (2H, m), 3.86 (3H, m), 3.89 (3H, s), 4.07 (1H, t, J=8.8 Hz), 4.88 (1H, m), 6.79 (1H, t, J=9.2 Hz), 6.99 (1H, m), 7.08 (1H, dd, J=2, 8.8 Hz), 7.36 (2H, m), 7.50 (1H, d, J=9.2 Hz), 7.59 (1H, m), 8.0 (1H, s).

HPLC (t, %): 7.9 min, 98%.
MS (ESI) m/z=511 (M+1)

Example 4

7-methoxy-2-methyl-N-[[(5S)-3-[3-fluoro-4-(4-morpholinyl)phenyl]-2-oxo-5-oxazolidinyl]methyl]-3-quinolinecarboxithioamide

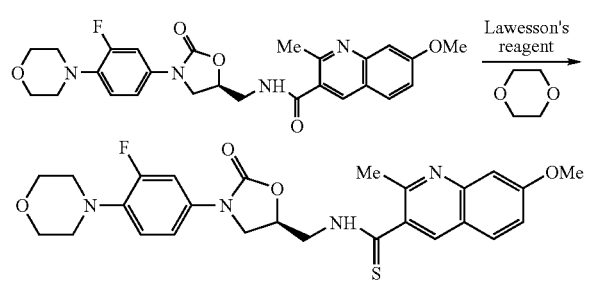

A solution of 50 mg of N-[[(5S)-3-[3-fluoro-4-(4-morpholinyl)-phenyl]-2-oxo-5-oxazolidinyl]methyl]-7-methoxy-2-methylquinoline-3-yl-amide, 123 mg (3 eq) of Lawesson's reagent in 4 mL of 1,4-dioxane was heated at 65° C. for 3 hours and at 100° C. for 1 h. The solvent was removed under reduced pressure and the crude was purified by column chromatography (Merck silica gel, Ethyl acetate/Hexane 99/1) to afford 39 mg of the title product (Yield=75%).

HPLC (t, %): 11.2 min, 96%.
MS (ESI) m/z=511 (M+1)

Example 5

7-methoxy-2-methyl-N-[[(5S)-3-[3-fluoro-4-(4-thiomorpholinyl)phenyl]-2-oxo-5-oxazolidinyl]methyl]-3-quinolinecarboxithioamide

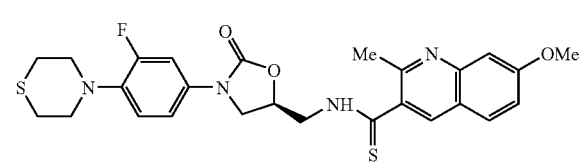

A solution of 50 mg of N-[[(5S)-3-[3-fluoro-4-(4-thiomorpholinyl)-phenyl]-2-oxo-5-oxazolidinyl]methyl]-7-methoxy-2-methylquinoline-3-yl-amide, 149 mg (4 eq) of Lawesson's reagent in 4 mL of 1,4-dioxane was heated at 65° C. for 3 hours and at 100° C. for 1 h. The solvent was removed under reduced pressure and the crude was purified by two sequential column chromatography (Merck silica gel, first column eluted with DCM/MeOH 95/5 and the second with Ethyl acetate) to afford 20 mg of the title product in a 99% purity (Yield=50%).

HPLC (t, %): 13.8 min, 99%.
MS (ESI) m/z=527 (M+1)

Example 6

7-methoxy-2-methyl-N-[[(5S)-3-[3-fluoro-4-(4'-thioacetyl-4-piperazinyl)-phenyl]-2-oxo-5-oxazolidinyl]methyl]-3-quinolinecarboxithioamide

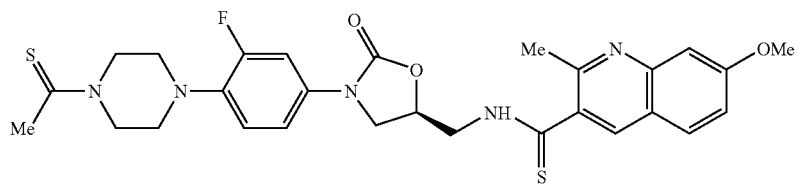

A solution of 50 mg of N-[[(5S)-3-[3-fluoro-4-(4'-acetyl-4-piperazinyl)phenyl]-2-oxo-5-oxazolidinyl]methyl]-7-methoxy-2-methylquinoline-3-yl-amide, 113 mg (3 eq) of Lawesson's reagent in 4 mL of 1,4-dioxane was heated at 65° C. for 3 hours and at 100° C. for 1 h. The solvent was removed under reduced pressure and the crude was purified by column chromatography (Merck silica gel, Ethyl acetate/Hexane 8/2) to afford 27 mg of the title product (Yield=53%).

HPLC (t, %): 12.3 min, 90%.
MS (ESI) m/z=568 (M+1)

Example 7

7-methoxy-2-methyl-N-[[(5S)-3-[3-fluoro-4-(1-oxothiomorpholin-4-yl)-phenyl]-2-oxo-5-oxazolidinyl]methyl]-3-quinolinecarboxamide

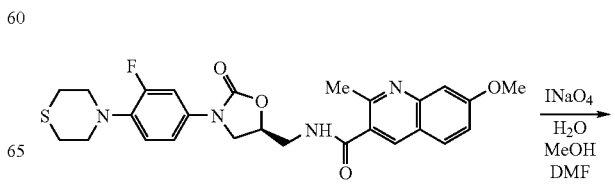

-continued

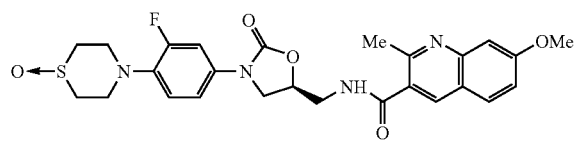

400 mg (10 eq) of sodium metaperiodate were dissolved in 1 mL of water and then cooled to 0° C. (ice bath). Next 100 mg (1 eq) of N-[[(5S)-3-[3-fluoro-4-(4-thiomorpholinyl)-phenyl]-2-oxo-5-oxazolidinyl]methyl]-7-methoxy-2-methylquinoline-3-yl-amide in 2.5 mL of methanol were added. 0.5 mL of DCM were added to increase solubility. The reaction was stirred at 0° C. for 3 hours until TLC showed complete conversion of the starting material. The crude mixture was transferred to a separatory funnel, DCM and water were added until having two clear layers, the organic layer was separated and the water layer was further extracted with DCM. The organic layers were combined, dried over $MgSO_4$, filtered and concentrated under reduced pressure to yield 95 mg. This solid was purified by column chromatography (10 g of silica gel, DCM/MeOH in increasing polarity) to give 82 mg (Yield=79%) of the title compound.

$^1$H NMR (400 MHz, δ, ppm, $CDCl_3$): 2.67 (3H, s), 2.88 (4H, m), 3.13 (2H, m), 3.56 (2H, m), 3.83 (3H, m), 3.89 (3H, s), 4.05 (1H, t, J=8 Hz), 4.88 (1H, m), 6.87 (1H, t, J=8.8 Hz), 6.92 (1H, d, J=8.8 Hz), 7.07 (1H, d, J=9.9 Hz), 7.44 (3H, m), 7.95 (1H, s).

HPLC (t, %): 6.80 min, 100%.
MS (ESI) m/z=527 (M+1)

Example 8

7-methoxy-2-methyl-N-[[(5S)-3-[3-fluoro-4-(1,1-dioxothiomorpholin-4-yl)-phenyl]-2-oxo-5-oxazolidinyl]methyl]-3-quinolinecarboxamide

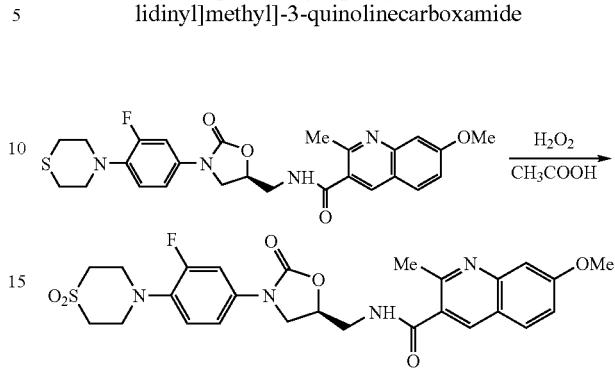

A solution of 388 mg (1 eq) of N-[[(5S)-3-[3-fluoro-4-(4-thiomorpholinyl)phenyl]-2-oxo-5-oxazolidinyl]methyl] 7-methoxy-2-methylquinoline-3-yl-amide in 20 mL of acetic acid and 1.05 mL (12 eq) of $H_2O_2$ 30% was stirred under reflux overnight. TLC of the crude mixture showed starting material left and 0.5 mL of $H_2O_2$ 30% was added and stirred overnight under reflux. The solvent was evaporated, dissolved in DCM and washed with saturated solution of $NaHCO_3$, the organic layers were dried with $Na_2SO_4$ and concentrated to give 190 mg. This was purified by column chromatography (10 g of silica gel, DCM/MeOH in increasing polarity) yielding 33 mg (Yield=8%) of the title compound.

$^1$H NMR (400 MHz, δ, ppm, $CDCl_3$): 2.69 (3H, s), 3.17 (4H, m), 3.52 (4H, m), 3.86 (3H, m), 3.9 (3H, s), 4.08 (1H, t, J=8 Hz), 4.9 (1H, m), 6.88 (1H, t, J=8 Hz), 7.02 (1H, m), 7.10 (1H, d, J=8.4 Hz), 7.27 (1H, m), 7.43 (1H, m), 7.53 (1H, m), 7.97 (1H, s).

HPLC (t, %): 8.7 min, 85%.
MS (ESI) m/z=543 (M+1)

The compounds of Table 1 below were prepared following same procedure as in Example 1:

TABLE 1

| Ex. | Structure | HPLC t(min), (%) | MS(ESI) m/z |
|---|---|---|---|
| 9 | 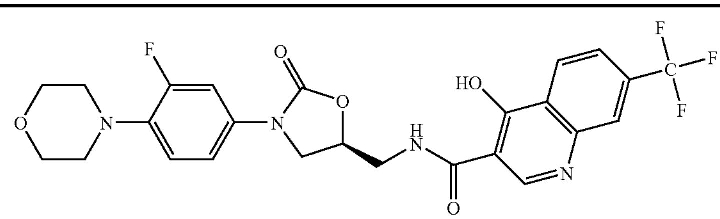 | 8.6 (88) | 338 |
| 10 | 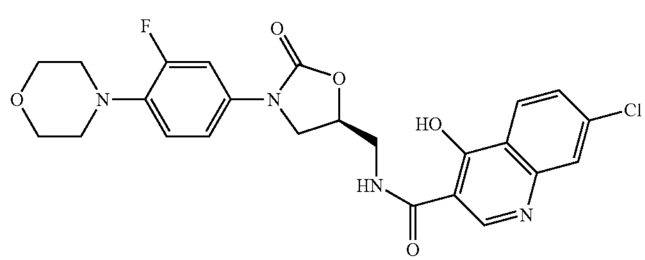 | 10.2 (90) | 501 |

TABLE 1-continued

| Ex. | Structure | HPLC t(min), (%) | MS(ESI) m/z |
|---|---|---|---|
| 11 | 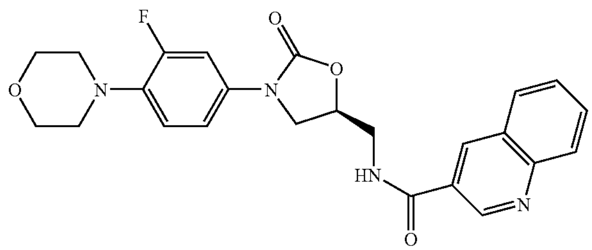 | 8.9 (100) | 451 |
| 12 | 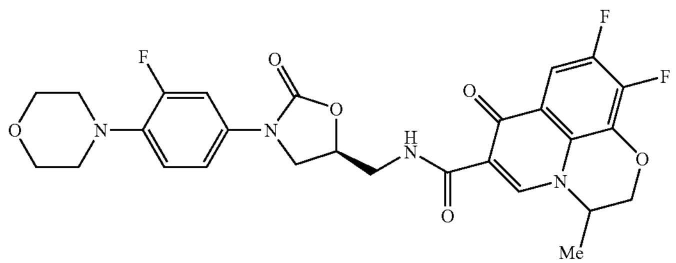 | 5.85 (93) | 559 |
| 13 | 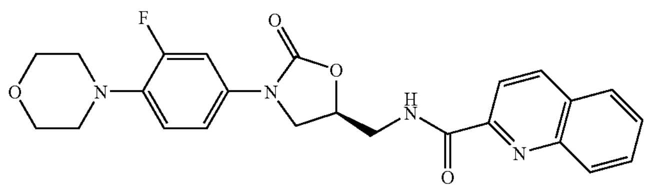 | 5.91 (92) | 451 |
| 14 | 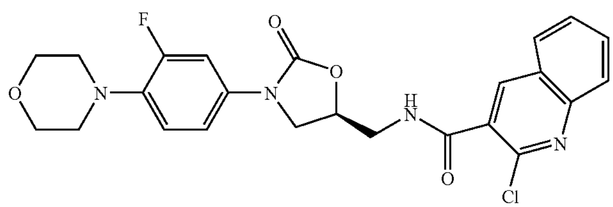 | 5.05 (88) | 485 |
| 15 | 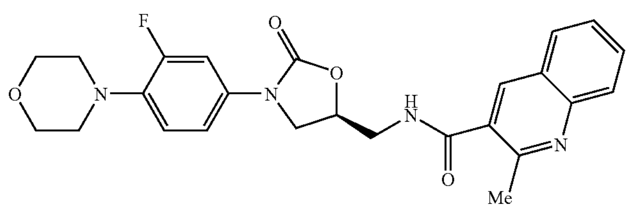 | 4.39 (98) | 465 |
| 16 | 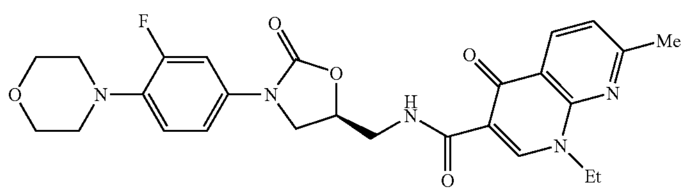 | 5.41 (99) | 510 |
| 17 | 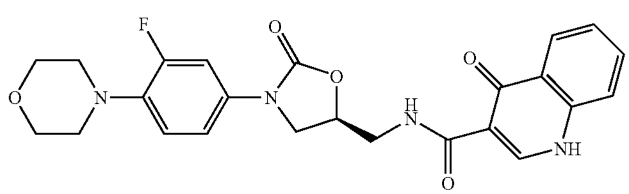 | 4.08 (95) | 467 |

TABLE 1-continued

| Ex. | Structure | HPLC t(min), (%) | MS(ESI) m/z |
|---|---|---|---|
| 18 | 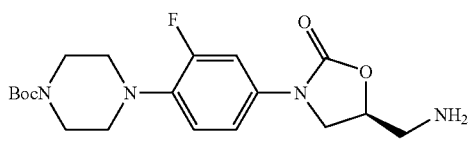 | 4.6 (100) | 495 |

Example 19

N-[(5S)-[3-[3-fluoro-4-[(N-t-butoxycarbonyl)piperazin-1-yl]phenyl]-2-oxo-5-oxazolidinylmethyl]amine

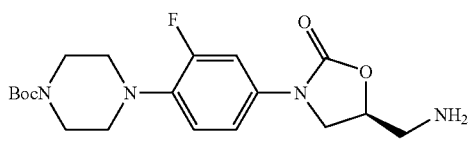

This compound can be obtained by two procedures:

Procedure A: To a solution of (S)-[3-[3-fluoro-4-[N-t-butoxycarbonylpiperazin-1-yl]phenyl]-2-oxooxazolidin-5-yl-methyl]azide (27.6 mmol) in EtOAc, 10% Pd/C (6.4 gr) was added and the reaction was allowed to stir at ambient temperature under $H_2$. The reaction was monitored by TLC, and when completion was reached, the mixture was filtered through celite and concentrated under vacuum. The purity of the crude product, which was kept under argon to avoid amine oxidation, was higher than 95%.

Procedure B: To a solution of (5S)-[3-[3-fluoro-4-[N-t-butoxycarbonylpiperazin-1-yl]phenyl]-2-oxooxazolidin-5-ylmethyl]alcohol (74.1 g, 0.19 mol) and triethylamine (36 mL, 0.26 mol) in DCM (750 mL) was added slowly 3-nitrobenzenesulfonyl chloride (55.6 g, 0.25 mol). The reaction was stirred for 24 hours, then washed with water (500 mL), dried and evaporated to give (5S)-[3-[3-fluoro-4-[N-t-butoxycarbonylpiperazin-1-yl]phenyl]-2-oxooxazolidin-5-ylmethyl]nosylate (116 gr) containing some unreacted 3-nitrobenzenesulfonyl chloride. To a solution of the nosylate (115 gr) in acetonitrile (2 L) was added concentrated ammonia (d=0.88, 100 mL) and the reaction mixture was heated to 40° C. for 3 hours. A second portion of ammonia (500 mL) was added and the mixture maintained at 40° C. overnight. A third portion of ammonia (500 mL) was added, followed 8 hours later by a final portion of ammonia (500 mL) and further stirring overnight. The reaction mixture was cooled, split into two portions, and each half diluted with water (1 L) and extracted with DCM (2×1 L). The combined DCM extracts were dried and evaporated to give 71.4 g of the desired product.

$^1$H NMR (400 MHz, δ, ppm, CD$_3$OD): 1.48 (9H, s), 2.96 (6H, m), 3.57 (4H, m), 3.81 (1H, m), 4.09 (1H, t, J=16 Hz), 4.7 (1H, m), 7.05 (1H, t, J=8 Hz), 7.19 (1H, m), 7.51 (1H, dd, J=2.4, 14 Hz).

HPLC (t, %): 4.8 min, 97%.

MS (ESI) m/z=395 (M+1)

Example 20

7-methoxy-2-methyl-N-[[(5S)-[3-[3-fluoro-4-[(N-t-butoxycarbonyl)piperazin-1-yl]phenyl]-2-oxo-5-oxazolidinylmethyl]-3-quinolinecarboxamide

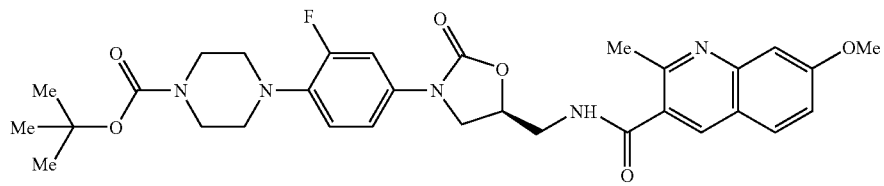

A mixture of 7-methoxy-2-methylquinoline-3-carboxylic acid (1.24 g, 5.72 mmol), EDCl (1.09 g, 5.72 mmol), DMAP (0.23 g, 1.9 mmol) and DCM (30 mL) was stirred for 30 minutes, then a solution of N-[(5S)-[3-[3-fluoro-4-[(N-t-butoxycarbonyl)piperazin-1-yl]phenyl]-2-oxo-5-oxazolidinylmethyl]amine (1.5 g, 3.81 mmol) in DCM was added. After stirring overnight, the mixture was washed with 5% acetic acid solution, saturated NaHCO$_3$, and finally brine. The solvent was evaporated under reduced pressure to give 2.1 g of desired product (93% yield).

$^1$H NMR (400 MHz, δ, ppm, CDCl$_3$): 1.47 (9H, s), 2.74 (3H, s), 2.96 (4H, m), 3.57 (4H, m), 3.9 (3H, m), 4.12 (1H, t, J=9 Hz), 4.9 (1H, m), 6.63 (1H, NH), 6.88 (1H, t, J=9 Hz), 7.06 (1H, m), 7.15 (1H, dd, J=2.4, 9.2 Hz), 7.32 (1H, m), 7.44 (1H, dd, J=3, 14 Hz), 7.59 (1H, d, J=9 Hz), 8.0 (1H, s).

HPLC (t, %): 6.6 min, 93%.

MS (ESI) m/z=594 (M+1)

Example 21

7-methoxy-2-methyl-N-[[(5S)-[3-[3-fluoro-4-(piperazin-1-yl)phenyl]-2-oxo-5-oxazolidinylmethyl]-3-quinolinecarboxamide

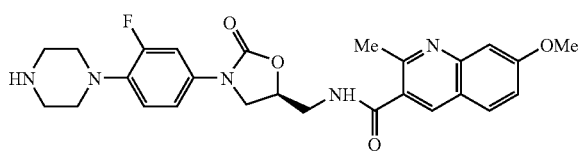

To a solution of Boc-protected derivative of example 20 in DCM (80 mL) at 0° C. was added a 50% solution of trifluoroacetic acid over 10 minutes. After 15 minutes, the mixture was allowed to warm up to room temperature and stirred overnight. The solvent was removed under reduced pressure and the residue dissolved in ethyl acetate (50 mL) before being extracted repeatedly with water (9×50 mL). The combined aqueous extracts were then taken to pH=12 ($K_2CO_3$), and extracted with ethyl acetate (9×50 mL). The organic extracts were dried and the solvent removed under reduced pressure to give the product as a white solid, yielding 1.6 g (60%).

Examples 22-27 and 37-42

(Table 2 below) were prepared following the same general procedure. The appropriate acid (0.21 mmol), EDCl.HCl (40 mg, 0.21 mmol), DMAP (8.5 mg, 70 mmol) and DMF (1.5 mL) were stirred for 30 minutes, then compound of Example 21 (70 mg, 0.14 mmol) was added. The mixture was stirred for approximately 64 hours, and ethyl acetate (6 mL) added. The mixture was washed with 5% acetic acid solution (3 mL), saturated $NaHCO_3$ solution (3 mL), and finally brine (3 mL). The organic phase was dried and the solvent was evaporated under reduced pressure to give the product.

Examples 28-33

(Table 2 below) were prepared following the same general procedure. To a mixture of the appropriate acid (0.24 mmol), compound of Example 21 (80 mg, 0.16 mmol) and DMF (2 mL) was added DMAP (10 mg, 0.08 mmol) and EDCl.HCl (46 mg, 0.24 mmol) (and in the case of Example 33 only, HOBt (31 mg, 0.24 mmol)). The solution was stirred overnight and diluted with DCM (4 mL). The mixture was washed with 5% acetic acid solution (2 mL), saturated $K_2CO_3$ solution (2 mL), and finally brine (2 mL). The organic phase was dried and the solvent was evaporated under reduced pressure to give the product, which was subsequently purified by flash chromatography.

Example 34-36

The procedure for compounds 22-27 was used, with quantities scaled up to 0.183 mmol of compound of Example 21.

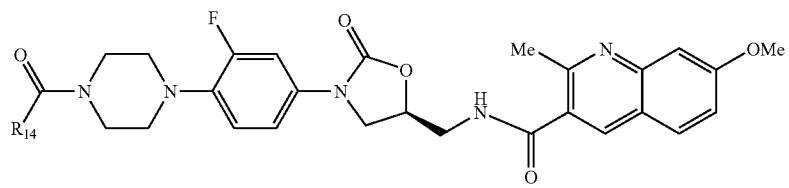

TABLE 2

| Ex. | $R_{14}$ | LC Purity | HPLC t(min) | MS(ESI) m/z |
|---|---|---|---|---|
| 22 | cyclobutyl | 95.1% | 11.6 | 576 |
| 23 | isopropenyl (CH2=C(Me)-) | 90.2% | 10.6 | 562 |
| 24 | vinyl (CH2=CH-) | 97.8% | 10.0 | 548 |
| 25 | MeOCH2- | 96.2% | 9.5 | 566 |
| 26 | MeOCH2CH2- | 97.8% | 9.7 | 580 |

TABLE 2-continued

| Ex. | R₁₄ | LC Purity | HPLC t(min) | MS(ESI) m/z |
|---|---|---|---|---|
| 27 | 6-oxo-1,6-dihydropyridazin-3-yl | 95.3% | 9.3 | 616 |
| 28 | pyrazin-2-yl | 95.8% | 9.8 | 600 |
| 29 | 6-oxo-1,4,5,6-tetrahydropyridazin-3-yl | 93.5% | 9.3 | 618 |
| 30 | 1H-pyrazol-4-yl | 89.4% | 9.2 | 588 |
| 31 | 1H-imidazol-4-yl | 84.5% | 7.9 | 588 |
| 32 | thiophen-3-yl | 90.6% | 11.3 | 604 |
| 33 | (S)-5-oxopyrrolidin-2-yl | 91.3% | 8.9 | 605 |
| 34 | cyclopropyl | 97.9% | 10.6 | 562 |
| 35 | HOCH₂- | 91.2% | 9.1 | 552 |
| 36 | (S)-1,2-dihydroxyethyl (HOCH₂-CH(OH)-) | 91.3% | 8.6 | 582 |
| 37 | Me₂CHCH₂- (isobutyl) | 96% | 5.35 | 578 |
| 38 | pyridin-4-yl | 92% | 4.1 | 599 |
| 39 | Me₂CH- (isopropyl) | 85% | 4.9 | 564 |
| 40 | CH₂CN | 94% | 4.2 | 561 |
| 41 | isoxazol-5-yl | 80% | 4.7 | 589 |
| 42 | pyridin-3-yl | 87% | 4.1 | 599 |

Example 43

Determination of Biological Data (a) Antibacterial Activity

Minimum inhibitory activities (MICs) were determined by using a standard microdilution method according to The National Committee for Clinical Laboratory Standards (NC-CLS), 5$^{th}$ Approved standard M7-A5, 2001, Wayne, Pa., USA.

All compounds were tested against Gram-positive and Gram-negative bacteria showing relevant different susceptibility and resistance specificity. The used microorganisms were selected from laboratory reference bacteria and from clinical isolates.

The tested concentrations were double dilutions from 0.06 μg/mL to 128 μg/mL in 96-well microtiter plates.

The microorganisms used in the study were:

Aerobic Gram-positive bacteria, consisting of *Staphylococcus aureus*, *Staphylococcus epidermidis*, *Enterococcus faecalls*, *Enterococcus faecium* and *Streptococcus pneumoniae*; and *Moraxella catarrhalis*, a Gram-negative bacterium, which is relevant to respiratory infections; it is also called fastidious because of its growing requirements.

MICs were determined in the *Brucella* Blood medium supplemented for the anaerobic strains, and in the Mueller-Hinton culture medium (cation-adjusted) for the aerobic bacteria.

The tested compounds were dissolved in DMSO, and were diluted as far as 2560 μg/mL with the different media according to the specific requirements for each group of strains.

The 96-well sealed microtiter plates containing bacteria were incubated in different laboratory conditions depending on the nature of the microorganism. Thus, the aerobic bacteria were incubated during 16-24 h at 35° C. and the so-called fastidious bacteria, such as *M. catarrhalis* and *S. pneumoniae*, during 20-24 h at 35° C. in a microaerobiotic atmosphere containing 5% $CO_2$ (Anaerocult C, MERCK).

(b) In Vitro MAO-A and MAO-B Enzymatic Activity

MAO-A and MAO-B enzymatic activities were measured using membranes obtained from SF9 cells expressing either human MAO-A or human MAO-B (Gentest, BD, USA). Assays were done in black 96-well microtiter plates using kynuramine as substrate and measuring the formation of 4-hydroxyquinoline by fluorescence at 340 nm/465 nm. Briefly, membranes with MAO-A (0.006 mg/mL protein) and MAO-B (0.015 mg/mL protein) were incubated with kynuramine, 30 μM, at 37° for 40 min in the presence of the compound in a final volume of 200 μL. Reactions were stopped by adding NaOH 2N and the reaction product, 4-hydroxyquinoline, was determined by fluorometry using a Tecan Ultra reader.

A low $K_i$ value indicates that the tested inhibitor possesses a tight binding ability to MAO enzyme, thus, it is a strong MAO inhibitor.

Antibacterial activity and MAO-A and MAO-B enzymatic activities are shown in Tables 3 and 4 respectively.

TABLE 3

In vitro activities against bacteria, MIC (μg/mL)

| Organism | Ex. 8 | Ex. 31 | Ex. 34 | Ex. 42 | Linezolid |
|---|---|---|---|---|---|
| S. aureus ATCC 25923 MS 319 | 2.00 | 4.00 | 0.50 | 1.00 | 2.00 |

TABLE 3-continued

In vitro activities against bacteria, MIC (μg/mL)

| Organism | Ex. 8 | Ex. 31 | Ex. 34 | Ex. 42 | Linezolid |
|---|---|---|---|---|---|
| S. aureus ATCC 43300 MR 214 | 2.00 | 2.00 | 0.50 | 0.06 | 1.00 |
| S. epidermidis ATCC 12228 MR 11 | 2.00 | 2.00 | 0.50 | 0.5 | 1.00 |
| S. pneumoniae ATCC 49619 PR 215 | 1.00 | 4.00 | 0.50 | 1.00 | 2.00 |

TABLE 4

Inhibitory activity of human MAO

| | Ex. 34 | Ex. 42 | Linezolid | Toloxatone |
|---|---|---|---|---|
| MAO-A % inh (10 μM) | 7 | 5 | 41 | 77 |
| MAO-B % inh (1 μM) | 8 | 7 | 62 | 7 |

(c) Selective Activity in *Staphylococcus* Bacteria Compared with *Enterococcus* Bacteria:

The results obtained are shown in the tables below:

1. Compounds with the Formula:

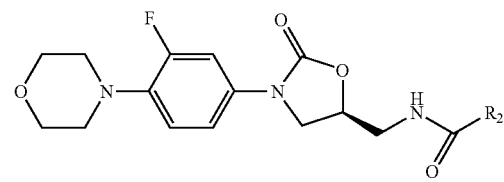

TABLE 5a

| | $R_2$ | Geometric Mean MIC Staphylococcus (μg/mL) | Geometric Mean MIC Enterococcus | Selectivity Enterococcus/ Sthaphylococcus |
|---|---|---|---|---|
| Ex. 1 | 2,3-dimethyl-7-methoxyquinoline | 0.6 | 5.7 | 9.5 |
| Ex. 18 | 2,3-dimethyl-6-methoxyquinoline | 1.0 | 8.0 | 8.0 |
| Comparartive Example 1 | 2-methylbenzofuran | 5.7 | 4.8 | 0.8 |

TABLE 5a-continued

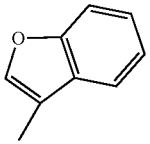

| R₂ | Geometric Mean MIC Staphylococcus (μg/mL) | Geometric Mean MIC Enterococcus | Selectivity Enterococcus/ Sthaphylococcus |
|---|---|---|---|
| Comparative Example 2 | 12.7 | 3.4 | 0.3 |
| Comparative Example 3 | 0.8 | 0.7 | 0.9 |
| Comparative Example 4 | 6.7 | 4.8 | 0.7 |
| Comparative Example 5 | 4.0 | 4.0 | 1.0 |

2. Compounds with the Formula:

TABLE 5b

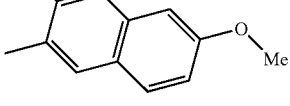

| R₂ | Geometric Mean MIC Sthaphylococcus (μg/mL.) | Geometric Mean MIC Enterococcus | Selectivity Enterococcus/ Sthaphylococcus |
|---|---|---|---|
| Ex. 3 | 0.4 | 5.7 | 14.3 |
| Comparative Example. 6 | 6.3 | 5.7 | 0.9 |

TABLE 5b-continued
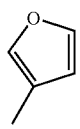
| R₂ | Geometric Mean MIC Sthaphylococcus (µg/mL.) | Geometric Mean MIC Enterococcus | Selectivity Enterococcus/ Sthaphylococcus |
|---|---|---|---|
| Comparative Example 7 | 4.0 | 2.5 | 0.6 |
3. Compounds with the Formula:
TABLE 5c
| R₂ | Geometric Mean MIC Sthaphylococcus (µg/mL.) | Geometric Mean MIC Enterococcus | Selectivity Enterococcus/ Sthaphylococcus |
|---|---|---|---|
| Ex. 24 | 0.6 | 16.0 | 27.0 |
| Comparative Example 8 | 4.8 | 3.2 | 0.66 |

4. Compounds with the Formula:

TABLE 5d

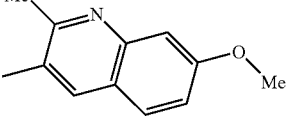

| R₂ | Geometric Mean MIC Sthaphylococcus (μg/mL. | Geometric Mean MIC Enterococcus | Selectivity Enterococcus/ Sthaphylococcus |
|---|---|---|---|
| Ex. 29 |  | 1.7 | 32.0 | 18.8 |
| Comparative Example 9 | 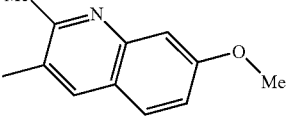 | 13.5 | 4.0 | 0.3 |

5. Compounds with the Formula:

TABLE 5e

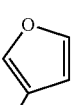

| R₂ | Geometric Mean MIC Sthaphylococcus (μg/mL. | Geometric Mean MIC Enterococcus | Selectivity Enterococcus/ Sthaphylococcus |
|---|---|---|---|
| Ex. 34 | (Me-quinoline-OMe) | 0.4 | 40.3 | 100 |
| Comparative Example 10 | (furan) | 6.7 | 4.0 | 0.6 |

6. Compounds with the Formula:

TABLE 5f

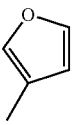

| R₂ | | Geometric Mean MIC Sthaphylo-coccus (μg/mL. | Geometric Mean MIC *Enterococcus* | Selectivity *Enterococcus/ Sthaphyloco-ccus* |
|---|---|---|---|---|
| Ex. 35 | Me, N / Me (quinoline) | 0.6 | 5.0 | 8.3 |
| Comparative Example 11 | furan | 4.8 | 3.2 | 0.7 |

These results show that compounds of the present invention display a selective activity against *Staphylococcus* bacteria in comparison with *Enterococcus* bacteria.

Example 44

Pharmaceutical Compositions

The following illustrate representative pharmaceutical compositions containing a compound of formula (I) or a pharmaceutically acceptable salt thereof for antimicrobial use in human or animals:

| Tablet 1 | mg/tablet |
|---|---|
| Active ingredient | 100 |
| Lactose | 179 |
| Croscarmellose sodium | 12 |
| Polyvinylpyrrolidone | 6 |
| Magnesium stearate | 3 |

| Tablet 2 | mg/tablet |
|---|---|
| Active ingredient | 50 |
| Lactose | 229 |
| Croscarmellose sodium | 12 |
| Polyvinylpyrrolidone | 6 |
| Magnesium stearate | 3 |

| Tablet 3 | mg/tablet |
|---|---|
| Active ingredient | 1 |
| Lactose | 92 |
| Croscarmellose sodium | 4 |
| Polyvinylpyrrolidone | 2 |
| Magnesium stearate | 1 |

| Capsule | mg/capsule |
|---|---|
| Active ingredient | 10 |
| Lactose | 389 |
| Croscarmellose sodium | 100 |
| Magnesium stearate | 1 |

| Injection | 50 mg/mL |
|---|---|
| Active ingredient | 5.0% w/v |
| Isotonic aqueous solution | to 100% |

Buffers, pharmaceutically acceptable co-solvents such as polyethylene glycol, polypropylene glycol, glycerol or ethanol or chelating agents, may be used to aid formulation.

The above formulations may be prepared by well-known conventional procedures in the pharmaceutical art. The tablets 1-3 may be enteric coated by conventional means, for example to provide a coating of cellulose acetate phthalate.

The invention claimed is:

1. A compound of formula (I):

(I)

wherein
R$_1$, R$_2$, R$_3$ and R$_4$ are independently selected from —H and halogen;
A is selected from the group consisting of (i)

(ii)

(iii)

(iv)

(v)

(vi)

(vii)

(viii)

(ix)

(x)

(xi)

(xii)

(xiii)

(xiv)

(xv)

(xvi)

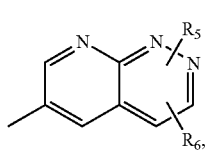 (xvii)

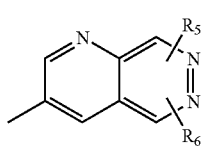 (xviii)

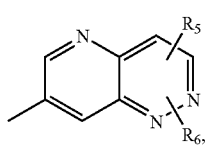 (xix)

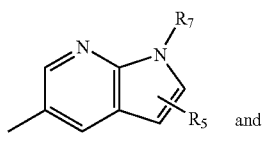 (xx)

and

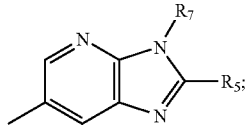 (xxi)

$R_5$ and $R_6$ are independently selected from the group consisting of —H, —F, —Cl, —Br, —OH, —NO$_2$, —CN, —CF$_3$, —COR$_8$, —CSR$_8$, —SO$_2$R$_8$, —OCOR$_8$, alkyl(C$_1$-C$_6$), haloalkyl(C$_1$-C$_6$), cycloalkyl(C$_3$-C$_6$), alkenyl(C$_2$-C$_6$), alkynyl(C$_2$-C$_6$), alkoxy(C$_1$-C$_6$), alkoxy(C$_1$-C$_6$)alkyl(C$_1$-C$_6$), —N—R$_{21}$R$_{22}$ and T; or R$_5$ and R$_6$ taken together form a benzo, pyrido, furo, thieno, oxazolo, isoxazolo, thiazolo, isothiazolo, pyrrolo, pyrazolo or imidazo fused-moiety, wherein said fused-moieties in turn may be substituted with one, two or three of the substituents selected from the group consisting of —F, —Cl, —Br, —OH, —NO$_2$, —CN, —CF$_3$, —COR$_8$, —CSR$_8$, —SO$_2$R$_8$, —OCOR$_8$, alkyl(C$_1$-C$_6$), haloalkyl(C$_1$-C$_6$), cycloalkyl(C$_3$-C$_6$), alkenyl(C$_2$-C$_6$), alkynyl(C$_2$-C$_6$), alkoxy(C$_1$-C$_6$), alkoxy(C$_1$-C$_6$)alkyl(C$_1$-C$_6$) and —N—R$_{21}$R$_{22}$, or a fused-ring selected from cyclopento, cyclohexo, cyclohepto, methylenedioxy and ethylenedioxy, wherein said fused-ring in turn may be substituted by one, two or three of the substituents selected from the group consisting of alkyl(C$_1$-C$_6$), cycloalkyl(C$_3$-C$_6$), alkenyl(C$_2$-C$_6$) and alkynyl(C$_2$-C$_6$);

R$_7$ is selected from the group consisting of —H, cycloalkyl (C$_3$-C$_6$), alkenyl(C$_2$-C$_6$), alkynyl(C$_2$-C$_6$), alkoxy(C$_1$-C$_6$), —N—R$_{21}$R$_{22}$, T and alkyl(C$_1$-C$_6$) wherein alkyl (C$_1$-C$_6$) is optionally substituted with one, two or three groups selected from the group consisting of —F, —Cl, —NO$_2$, —OR$_{21}$, —COR$_{21}$, —N—R$_{21}$R$_{22}$, oxo, cycloalkyl(C$_3$-C$_6$), alkenyl(C$_2$-C$_6$), alkynyl(C$_2$-C$_6$), —CN, T, —COO—R$_{21}$, —OCOR$_{21}$, —CON—R$_{21}$R$_{22}$, —N(R$_{21}$)—CO—R$_{22}$, —OCON—R$_{21}$R$_{22}$, and —N(R$_{21}$)—COO—R$_{22}$; or R$_7$ and R$_5$ or R$_6$ taken together form where possible a ring of 2 to 6 carbon atoms and containing from 1 to 3 groups selected from O, N, S, SO and SO$_2$, which in turn may be substituted by one, two or three of the substituents selected from the group consisting of alkyl(C$_1$-C$_6$), cycloalkyl(C$_3$-C$_6$), alkenyl(C$_2$-C$_6$) and alkynyl(C$_2$-C$_6$);

R$_8$ is selected from the group consisting of —H, alkyl(C$_1$-C$_6$), cycloalkyl(C$_3$-C$_6$), alkenyl(C$_2$-C$_6$), alkynyl(C$_2$-C$_6$), alkoxy(C$_1$-C$_6$), alkoxy(C$_1$-C$_6$)alkyl(C$_1$-C$_6$), hydroxyalkyl(C$_1$-C$_6$), —N—R$_{21}$R$_{22}$ and T;

R$_9$ and R$_{10}$ are independently selected from the group consisting of —H, —CN, —NO$_2$, —COR$_{11}$, —SO$_2$R$_{11}$, alkyl(C$_1$-C$_6$), haloalkyl(C$_1$-C$_6$), cycloalkyl(C$_3$-C$_6$), alkenyl(C$_2$-C$_6$), alkynyl(C$_2$-C$_6$), alkoxy(C$_1$-C$_6$), alkoxy (C$_1$-C$_6$)alkyl(C$_1$-C$_6$), —N—R$_{21}$R$_{22}$ and T;

R$_{11}$ is selected from the group consisting of —H, —OH, alkyl(C$_1$-C$_6$), haloalkyl(C$_1$-C$_6$), cycloalkyl(C$_3$-C$_6$), alkenyl(C$_2$-C$_6$), alkynyl(C$_2$-C$_6$), alkoxy(C$_1$-C$_6$)alkyl(C$_1$-C$_6$) and T;

R$_{12}$ and R$_{13}$ are independently selected from the group consisting of —H, —OH, —CHR$_{14}$R$_{15}$, —CN, —COR$_{14}$, —CSR$_{14}$, —COOR$_{14}$, —CSOR$_{14}$, —CONR$_{14}$R$_{15}$, —CSNR$_{14}$R$_{15}$, —CON(R$_{16}$)N(R$_{14}$)R$_{15}$, —SO$_2$R$_{14}$, —SO$_2$OR$_{14}$, —SO$_2$NR$_{14}$R$_{15}$, alkyl(C$_1$-C$_6$), haloalkyl(C$_1$-C$_6$), cycloalkyl(C$_3$-C$_6$), alkenyl(C$_2$-C$_6$), alkynyl(C$_2$-C$_6$), alkoxy(C$_1$-C$_6$)alkyl(C$_1$-C$_6$) and T;

R$_{14}$ and R$_{15}$ are independently selected from the group consisting of —H, —OH, —COR$_{16}$, —CSR$_{16}$, —SO$_2$R$_{16}$, —NR$_{17}$R$_{18}$, cycloalkyl(C$_3$-C$_6$), alkenyl(C$_2$-C$_6$), alkynyl(C$_2$-C$_6$), alkoxy(C$_1$-C$_6$), phenyl,

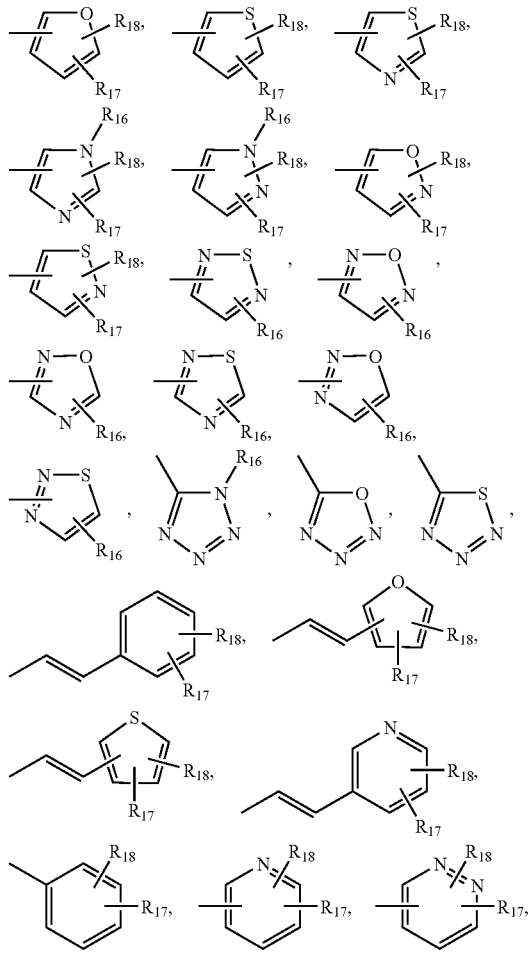

-continued

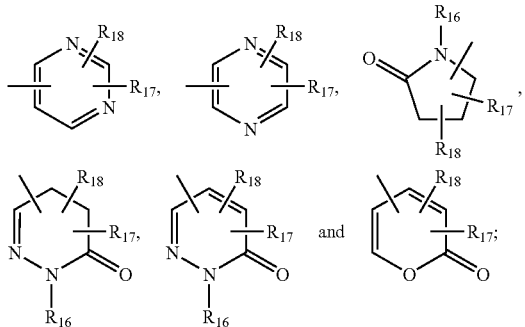

and alkyl($C_1$-$C_6$) wherein alkyl($C_1$-$C_6$) is optionally substituted with one, two or three groups selected from the group consisting of —F, —Cl, —NO$_2$, —OR$_{21}$, —COR$_{21}$, —N—R$_{21}$R$_{22}$, oxo, cycloalkyl($C_3$-$C_6$), alkenyl($C_2$-$C_6$), alkynyl($C_2$-$C_6$), —CN, T, —COO—R$_{21}$, —OCOR$_{21}$, —CON—R$_{21}$R$_{22}$, —N(R$_{21}$)—CO—R$_{22}$, —OCON—R$_{21}$R$_{22}$, and —N(R$_{21}$)—COO—R$_{22}$;

R$_{16}$ is —H, —OH, alkyl($C_1$-$C_6$), cycloalkyl($C_3$-$C_6$), alkenyl($C_2$-$C_6$), alkynyl($C_2$-$C_6$), alkoxy($C_1$-$C_6$), alkoxy($C_1$-$C_6$)alkyl($C_1$-$C_6$), hydroxyalkyl($C_1$-$C_6$) and T;

R$_{17}$ and R$_{18}$ are independently selected from the group consisting of —H, —OH, —F, —Cl, —Br, —NO$_2$, —CN, —NR$_{19}$R$_{20}$, —COR$_{19}$, —CONR$_{19}$R$_{20}$, —SO$_2$R$_{19}$, —SO$_2$NR$_{19}$R$_{20}$, cycloalkyl($C_3$-$C_6$), alkenyl ($C_2$-$C_6$), alkynyl($C_2$-$C_6$), alkoxy($C_1$-$C_6$), T and alkyl ($C_1$-$C_6$) wherein alkyl($C_1$-$C_6$) is optionally substituted with one, two or three groups selected from the group consisting of —F, —Cl, —NO$_2$, —OR$_{21}$, —COR$_{21}$—N—R$_{21}$R$_{22}$, oxo, cycloalkyl($C_3$-$C_6$), alkenyl($C_2$-$C_6$), alkynyl($C_2$-$C_6$), —CN, T, —COO—R$_{21}$, —OCOR$_{21}$, —CON—R$_{21}$R$_{22}$, —N(R$_{21}$)—CO—R$_{22}$, —OCON—R$_{21}$R$_{22}$, and —N(R$_{21}$)—COO13 R$_{22}$; or R$_{17}$ and R$_{18}$ taken together form a benzo-fused moiety, which in turn may be substituted with one, two or three of the substituents selected from the group consisting of —F, —Cl, —Br, —OH, —NO$_2$, —CN, —CF$_3$, —COR$_8$, —CSR$_8$, —SO$_2$R$_8$, —OCOR$_8$, alkyl($C_1$-$C_6$), haloalkyl($C_1$-$C_6$), cycloalkyl($C_3$-$C_6$), alkenyl($C_2$-$C_6$), alkynyl($C_2$-$C_6$), alkoxy($C_1$-$C_6$), alkoxy($C_1$-$C_6$)alkyl($C_1$-$C_6$) and —N—R$_{21}$R$_{22}$, or a fused-ring selected from cyclopento, cyclohexo, cyclohepto, methylenedioxy and ethylenedioxy, wherein said fused-ring in turn may be substituted by one, two or three of the substituents selected from the group consisting of alkyl($C_1$-$C_6$), cycloalkyl ($C_3$-$C_6$), alkenyl($C_2$-$C_6$) and alkynyl($C_2$-$C_6$);

R$_{19}$ and R$_{20}$ are independently selected from the group consisting of —H, —OH, cycloalkyl($C_3$-$C_6$), alkenyl ($C_2$-$C_6$), alkynyl($C_2$-$C_6$), alkoxy($C_1$-$C_6$), T and alkyl ($C_1$-$C_6$) wherein alkyl($C_1$-$C_6$) is optionally substituted with one, two or three groups selected from the group consisting of —F, —Cl, —NO$_2$, —OR$_{21}$, —COR$_{21}$, —N—R$_{21}$R$_{22}$, oxo, cycloalkyl($C_3$-$C_6$), alkenyl($C_2$-$C_6$), alkynyl($C_2$-$C_6$), —CN, T, —COO—R$_{21}$, —OCOR$_{21}$, —CON—R$_{21}$R$_{22}$, —N(R$_{21}$)—CO—R$_{22}$, —OCON—R$_{21}$R$_{22}$, and —N(R$_{21}$)—COO—R$_{22}$;

R$_{21}$ and R$_{22}$ are independently selected from —H, alkyl ($C_1$-$C_6$), cycloalkyl($C_3$-$C_6$), alkenyl($C_2$-$C_6$), alkynyl ($C_2$-$C_6$) and T, said —N—R$_{21}$R$_{22}$ groups may represent a heterocyclic ring selected from the group consisting of pyrrolidinyl, piperidinyl, piperazinyl optionally N-substituted by alkyl($C_1$-$C_6$), cycloalkyl($C_3$-$C_6$), alkenyl ($C_2$-$C_6$) or alkynyl($C_2$-$C_6$), morpholinyl, thiomorpholinyl, thiomorpholinyl S-oxide and thiomorpholinyl S-dioxide;

T represents a phenyl or heteroaryl group each optionally substituted, wherein heteroaryl is selected from the group consisting of pyridine, pyridazine, pyrimidine, pyrazine, furan, thiophene, oxazole, thiazole, imidazole, pyrazole, isoxazole, isothiazole, 1,2,5-thiadiazole, furazan, 1,2,4-oxadiazole, 1,2,4-thiadiazole, 1,2,3-oxadiazole, 1,2,3-thiadiazole, tetrazole, 1,2,3,4-oxatriazole and 1,2,3,4-thiatriazole, wherein substituents optionally present on the optionally substituted phenyl or optionally substituted heteroaryl group may be one, two or three of the substituents selected from the group consisting of —F, —Cl, —Br, —OH, —NH$_2$, —NO$_2$, —CN, —CF$_3$, —COR$_8$, —CSR$_8$, —SO$_2$R$_8$, —OCOR$_8$, alkyl ($C_1$-$C_6$), haloalkyl($C_1$-$C_6$), cycloalkyl($C_3$-$C_6$), alkenyl ($C_2$-$C_6$), alkynyl($C_2$-$C_6$), alkoxy($C_1$-$C_6$), alkoxy($C_1$-$C_6$)alkyl($C_1$-$C_6$), NH-alkyl($C_1$-$C_6$), NH-cycloalkyl($C_3$-$C_6$), —N—dialkyl($C_1$-$C_6$), —N—(alkyl($C_1$-$C_6$))(cycloalkyl($C_3$-$C_6$)), methylenedioxy, ethylenedioxy and a heterocyclic ring selected from the group consisting of pyrrolidinyl, piperidinyl, piperazinyl optionally N-substituted by alkyl($C_1$-$C_6$), cycloalkyl($C_3$-$C_6$), alkenyl($C_2$-$C_6$) or alkynyl($C_2$-$C_6$), morpholinyl, thiomorpholinyl, thiomorpholinyl S-oxide and thiomorpholinyl S-dioxide;

X is selected from O, S, NR$_9$ and CR$_9$R$_{10}$; and

Y is selected from NO and NR$_{12}$; and wherein the optional substituents of the alkyl($C_1$-$C_6$) groups might be one, two or three selected from the group consisting of —F, —Cl, —NO$_2$, OR$_{21}$, —COR$_{21}$, —N—R$_{21}$R$_{22}$, oxo, cycloalkyl($C_3$-$C_6$), alkenyl($C_2$-$C_6$), alkynyl($C_2$-$C_6$), —CN, T, —COO—R$_{21}$, —OCOR$_{21}$, —CON—R$_{21}$R$_{22}$, —N(R$_{21}$)—CO—R$_{22}$, —OCON—R$_{21}$R$_{22}$, and —N(R$_{21}$)—COO—R$_{22}$;

or a pharmaceutically acceptable salts thereof.

2. The compound according to claim 1, wherein R$_1$ is —F and R$_2$, R$_3$ and R$_4$ are each —H.

3. The compound according to claim 2, wherein X is O.

4. The compound according to claim 2, wherein X is S.

5. The compound according to claim 2, wherein X is N—CN.

6. The compound according to claim 2, wherein A is

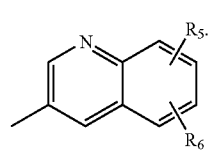

(i)

7. The compound according to claim 6, wherein R$_5$ and R$_6$ are each —H.

8. The compound according to claim 6, wherein R$_5$ is methyl and R$_6$ is methoxy.

9. The compound according to claim 6, wherein R$_5$ and R$_6$ are selected from the group consisting of —F, —Cl and —Br.

10. The compound according to claim 2, wherein A is

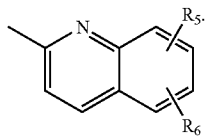
(ii)

11. The compound according to claim 10, wherein $R_5$ and $R_6$ are each —H.

12. The compound according to claim 10, wherein $R_5$ is methyl and $R_6$ is methoxy.

13. The compound according to claim 10, wherein $R_5$ and $R_6$ are selected from the group consisting of —F, —Cl and —Br.

14. The compound according to claim 2, wherein A is

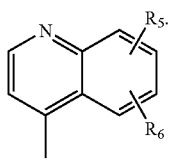
(iii)

15. The compound according to claim 14, wherein $R_5$ and $R_6$ are each —H.

16. The compound according to claim 14, wherein $R_5$ is methyl and $R_6$ is methoxy.

17. The compound according to claim 14, wherein $R_5$ and $R_6$ are selected from —F, —Cl and —Br.

18. The compound according to claim 2, wherein Y is $NR_{12}$.

19. The compound according to claim 18, wherein $R_{12}$ is selected from the group consisting of —H, methyl and ethyl.

20. The compound according to claim 18, wherein $R_{12}$ is selected from the group consisting of —CN, —COCH$_2$CN, —COCH$_3$, —COOCH$_3$, —CONHCH$_3$, —SO$_2$CH$_3$, —SOCH$_3$ and —SO$_2$NHCH$_3$.

21. The compound according to claim 18, wherein $R_{12}$ is

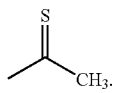

22. The compound according to claim 18, wherein $R_{12}$ is selected from the group consisting of

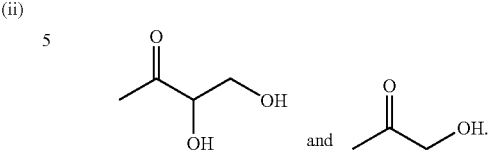

23. The compound according to claim 18, wherein $R_{12}$ is

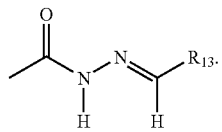

24. The compound according to claim 23, wherein $R_{13}$ is selected from the group consisting of —H, methyl, ethyl, isopropyl, tertbutyl, —CH$_2$OH, —CH$_2$NH$_2$, —COOH, —COOCH$_3$, —COOC$_2$H$_5$, —CH$_2$Cl, —CONH$_2$, —CH$_2$—CH=CH$_2$, —CH$_2$—C≡CH, —CH=CH$_2$, —C≡CH and —CH=CHN(CH$_3$)$_2$.

25. The compound according to claim 18, wherein $R_{12}$ is selected from the group consisting of

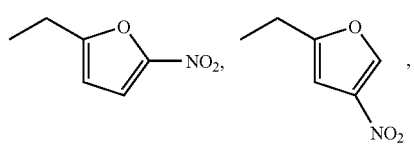

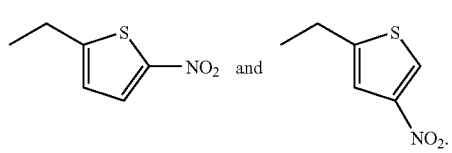

26. The compounds according to claim 1 which are the enantiomers having the S-configuration at C-5 position of the oxazolidinone ring.

27. The compound according to claim 2, which is of formula:

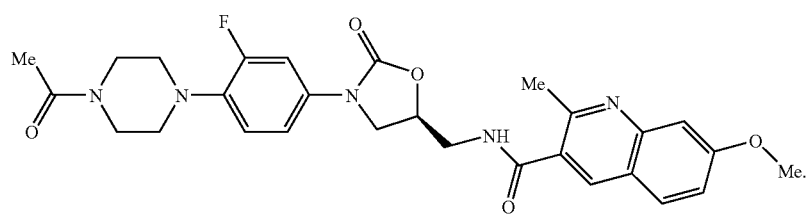

28. The compound according to claim 2, which is of formula:

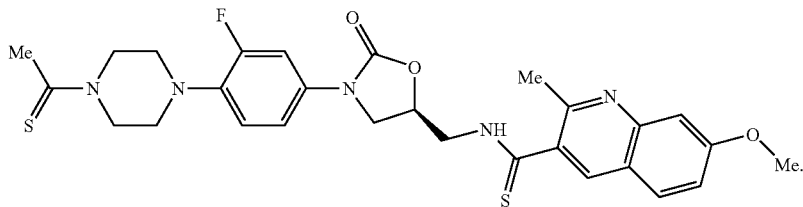

29. A method for the preparation of a compound of formula (I), when X is O, as defined in claim 1, which comprises acylating an amino methyl intermediate of formula (II):

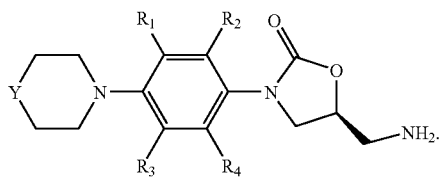

wherein $R_1$, $R_2$, $R_3$, $R_4$ and Y are as defined in the formula (I), with an activated form of the corresponding acid of formula (III):

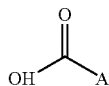

wherein A is as defined in the formula (I).

30. The method according to claim 29, wherein the activated form of the acid (III) is selected from the group consisting of acid halides, imidazolides, p-nitrophenyl esters and 2,4,5-trichlorophenyl esters thereof.

31. The method according to claim 29, wherein the activated form of the acid (III) is prepared in situ in the presence of a reagent selected from triphenylphosphine, bromotrichloromethane, dicyclohexylcarbodiimide, 2-chloropyridinium cation, 3-chloroisoxazolium cation, diphenylphosphoryl azide, N-hydroxybenzotriazole, 2-(1H-benzotriazole-1-yl)-1,1,3,3-tetramethyluronium hexafluorophosphate, 1-mesitylene-2-sulfonyl)-3-nitro-1H-1,2,4-triazole, benzotriazole-1-yl-oxy-trispyrrolidino-phosphonium hexafluorophosphate, 1-ethyl-3-(3'-dimethylaminopropyl)carbodiimide hydrochloride and 2-(1H-benzotriazole-1-yl)-1,1,3,3-tetramethyluronium tetrafluoroborate.

32. A method for the preparation of a compound of formula (I), when X is S, as defined in claim 1, which comprises reacting the corresponding compound of formula (I), when X is O, with a thionation reagent selected from:

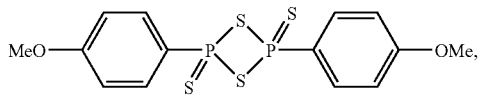

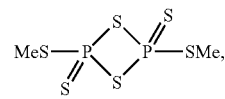

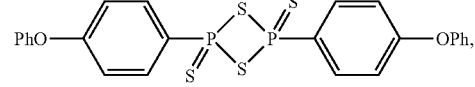

$P_4S_{10}$,                                    (IViv)

$Na_2P_4S_{11}$   and                           (IVv)

$Na_2P_4S_{10}O$.                               (IVvi)

33. The method according to claim 32 wherein the thionation reagent is the compound (IVi).

34. A method for the preparation of a compound of formula (I), when X is S, as defined in claim 1, which comprises reacting the corresponding amino methyl derivative (II):

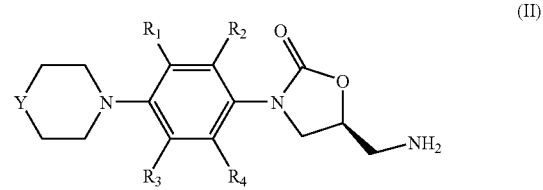

wherein $R_1$, $R_2$, $R_3$, $R_4$ and Y are as defined in the formula (I), with an alkyldithioamide (IIIi):

wherein A is as defined in the formula (I) and R is an alkyl($C_1$-$C_6$).

35. A method for the preparation of a compound of formula (I), when X is N—CN, as defined in claim 1, which comprises reacting an amino methyl intermediate of formula (II):

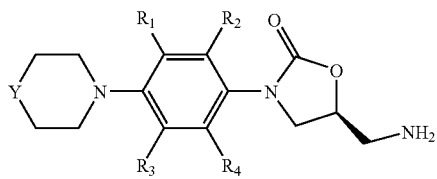

wherein $R_1$, $R_2$, $R_3$, $R_4$ and Y are as defined in the formula (I), with a cyanoimidate of formula (V):

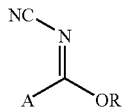

wherein A is as defined in the formula (I) and R is an alkyl($C_1$-$C_6$).

36. A method of treating bacterial infections in a human or animal wherein a compound as defined in claim 1 is administered to a human or animal.

37. A method according to claim 36, wherein the compound is administered by oral, parenteral, inhalatory, rectal, transdermal or topical route.

38. A method according to claim 36, wherein the compound is administered in an amount of 0.1 to 100 mg/kg of body weight/day.

39. A method according to claim 38, wherein the compound is administered in an amount of 1 to 50 mg/kg of body weight/day.

40. A pharmaceutical composition comprising a therapeutically effective amount of the compound of formula (I) as defined in claim 1, together with the appropriate amounts of pharmaceutical excipients or carriers.

* * * * *